United States Patent
Hanada et al.

(10) Patent No.: US 9,594,140 B2
(45) Date of Patent: Mar. 14, 2017

(54) MAGNETIC RESONANCE IMAGING APPARATUS AND METHOD FOR CALCULATING CORRECTION VALUE AS APPLICATION AMOUNT OF REFOCUSING PULSE FOR UTE SEQUENCE

(75) Inventors: Hikaru Hanada, Tokyo (JP); Kuniharu Oka, Tokyo (JP); Masaharu Ono, Tokyo (JP); Masahiro Takizawa, Tokyo (JP)

(73) Assignee: HITACHI, LTD., Tokyo (JP)

( * ) Notice: Subject to any disclaimer, the term of this patent is extended or adjusted under 35 U.S.C. 154(b) by 548 days.

(21) Appl. No.: 14/232,470

(22) PCT Filed: Aug. 21, 2012

(86) PCT No.: PCT/JP2012/071020
§ 371 (c)(1),
(2), (4) Date: Jan. 13, 2014

(87) PCT Pub. No.: WO2013/027710
PCT Pub. Date: Feb. 28, 2013

(65) Prior Publication Data
US 2014/0167752 A1 Jun. 19, 2014

(30) Foreign Application Priority Data
Aug. 23, 2011 (JP) .................................. 2011-181739

(51) Int. Cl.
*G01V 3/00* (2006.01)
*G01R 33/561* (2006.01)
(Continued)

(52) U.S. Cl.
CPC ............ *G01R 33/561* (2013.01); *A61B 5/055* (2013.01); *G01R 33/4816* (2013.01)

(58) Field of Classification Search
CPC .... G01R 33/561; G01R 33/4816; A61B 5/055
(Continued)

(56) References Cited

U.S. PATENT DOCUMENTS

| 4,812,760 A | * | 3/1989 | Bottomley | ........... G01R 33/446 324/309 |
| 5,126,673 A | * | 6/1992 | Hennig | .............. G01R 33/5615 324/309 |

(Continued)

FOREIGN PATENT DOCUMENTS

| JP | 2-211124 | 8/1990 |
| JP | 4-35539 | 5/1992 |

(Continued)

OTHER PUBLICATIONS

International Search Report in PCT/JP2012/071020, Nov. 2012.
(Continued)

*Primary Examiner* — Susan Lee
(74) *Attorney, Agent, or Firm* — Cooper & Dunham LLP

(57) ABSTRACT

In order to obtain a high-quality image even in multi-slice imaging in a UTE sequence that uses a half RF pulse, a refocusing pulse of the slice gradient magnetic field is adjusted and applied so that the excitation profiles of positive polarity data and negative polarity data have phase distributions that are 180 [deg] inverted with respect to each other in side lobe portions. In addition, the irradiation frequency of the half RF pulse is adjusted so as to eliminate a position shift between the intensity distributions of the positive polarity data and the negative polarity data.

20 Claims, 23 Drawing Sheets

(51) Int. Cl.
*A61B 5/055* (2006.01)
*G01R 33/48* (2006.01)

(58) Field of Classification Search
USPC .......................................................... 324/307
See application file for complete search history.

(56) References Cited

U.S. PATENT DOCUMENTS

| | | | |
|---|---|---|---|
| 6,256,526 B1* | 7/2001 | Butts | G01R 33/285 |
| | | | 324/307 |
| 7,479,783 B2* | 1/2009 | Alsop | G01R 33/5615 |
| | | | 324/307 |
| 2005/0127911 A1* | 6/2005 | Magland | G01R 33/483 |
| | | | 324/307 |
| 2011/0245655 A1 | 10/2011 | Abe et al. | |

FOREIGN PATENT DOCUMENTS

| | | |
|---|---|---|
| WO | WO2004/095049 | 11/2004 |
| WO | WO2010/074057 | 7/2010 |

OTHER PUBLICATIONS

C. Schroeder et al., "Slice Excitation for Ultrashort TE Imaging", Proc. Intl. Soc. Mag. Reson. Med. 12, 2004, 628.

M. Takizawa et al., "Correcting K-trajectory by Using Multiple Function Models of Gradient Waveform for Ultrashort TE (UTE)", Proc. Intl. Soc. Mag. Reson. Med. 19, 2011, 4385.

\* cited by examiner

FIG.7
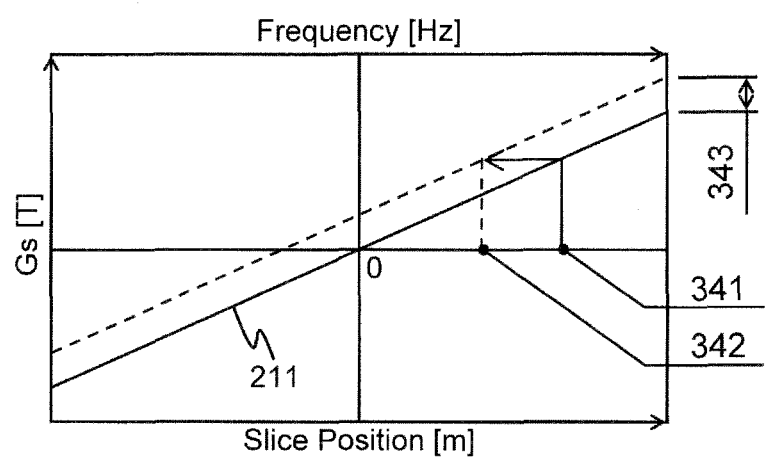
(a)
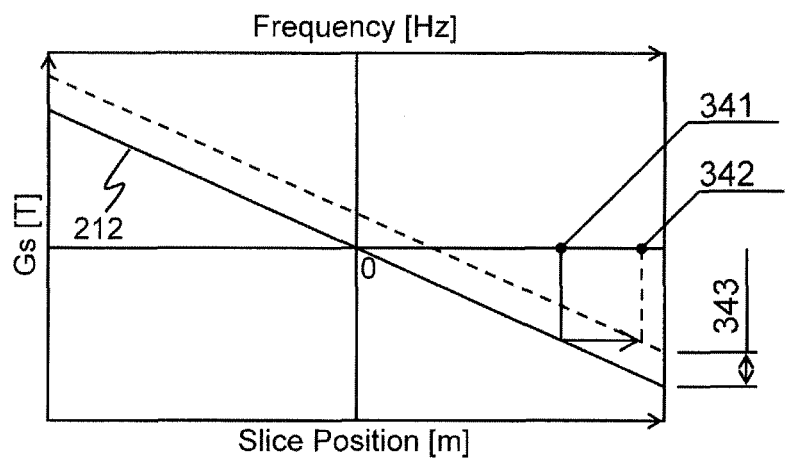
(b)

FIG.9
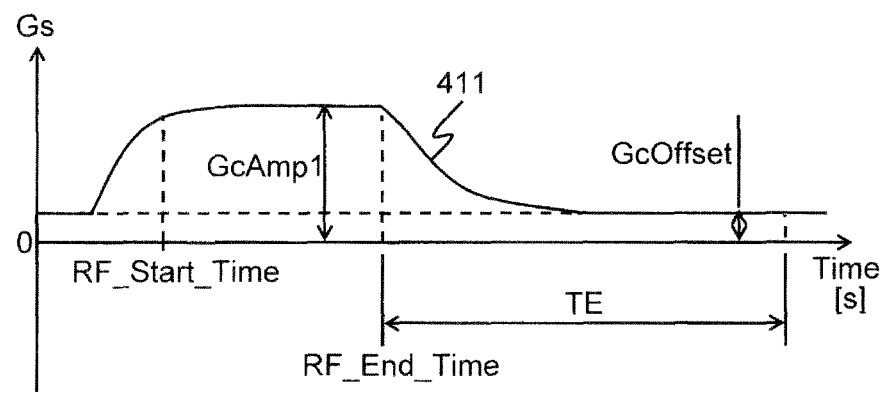
(a)
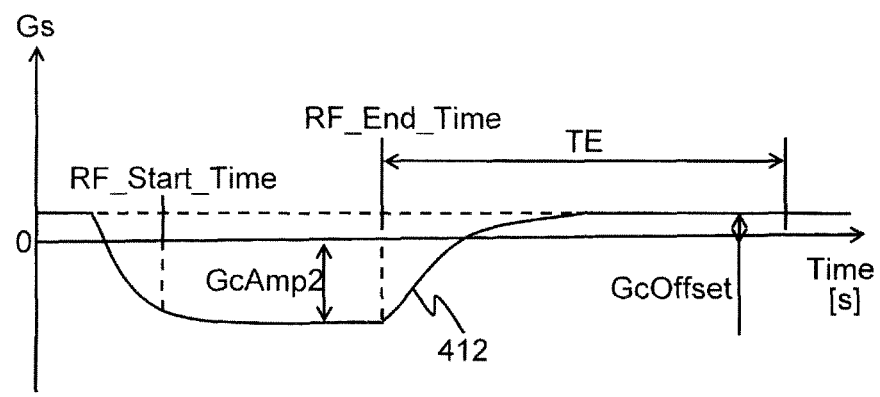
(b)

FIG.16
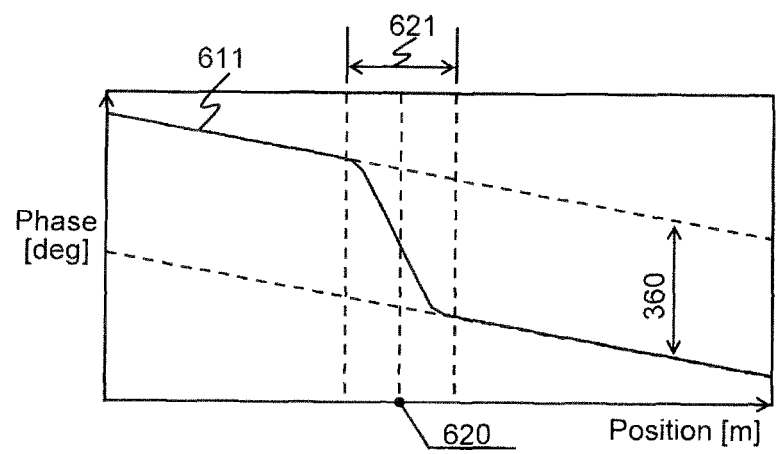
(a)
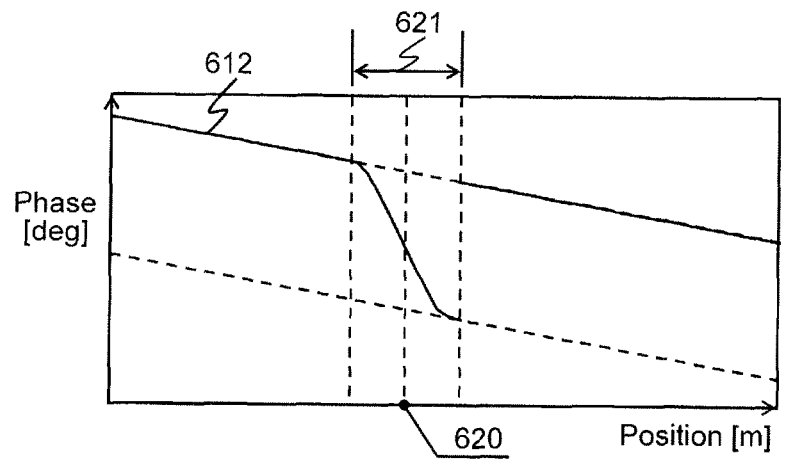
(b)

FIG.19
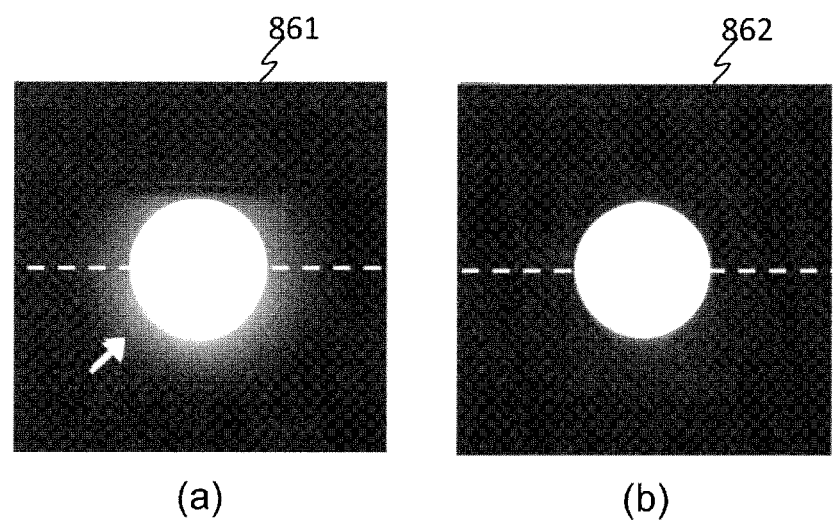
(a)                    (b)
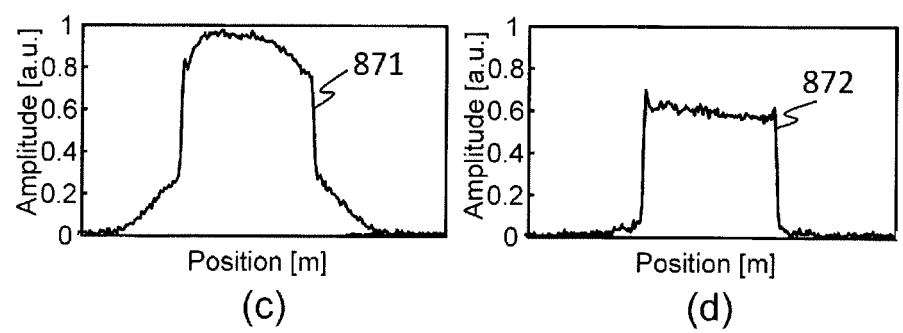
(c)                    (d)

MAGNETIC RESONANCE IMAGING APPARATUS AND METHOD FOR CALCULATING CORRECTION VALUE AS APPLICATION AMOUNT OF REFOCUSING PULSE FOR UTE SEQUENCE

TECHNICAL FIELD

The present invention relates to a magnetic resonance imaging (herein after, referred to as "MRI") apparatus that measures a nuclear magnetic resonance signal (hereinafter, referred to as an NMR signal) from hydrogen, phosphorus, or the like in an object and images nuclear density distribution, relaxation time distribution, or the like, and in particular, to an imaging technique using an ultra-short echo time sequence.

BACKGROUND ART

An MRI apparatus is an apparatus that measures an NMR signal (echo signal) generated by an object, especially, the nuclear spins that form human tissue, and images the shapes or functions of the head, abdomen, limbs, and the like in a two-dimensional manner or in a three-dimensional manner. In imaging, an object is disposed in a static magnetic field (polarized magnetic field BO), and then a slice selection gradient magnetic field pulse is applied together with a high frequency magnetic field pulse (RF pulse) in order to selectively excite a specific region and a phase encoding gradient magnetic field pulse or a readout gradient magnetic field pulse is applied for encoding within the excitation range, thereby giving the phase information.

The slice gradient magnetic field pulse generates a magnetic field inclined in an arbitrary direction, and generates a strength gradient of the magnetic field in static magnetic field space. The nuclear spins that form an object precess at a frequency corresponding to the gyromagnetic ratio and the strength of the inclined magnetic field. The frequency of the precession is called a Larmor frequency, and it is possible to excite only the nuclear spins at an arbitrary position by irradiating the RF pulse that matches the Larmor frequency.

In the case of an ideal state neglecting the relaxation phenomenon of nuclear spins, the excitation range and strength (hereinafter, referred to as an excitation profile) are a Fourier transform of the envelope of the RF pulse. The most common waveform of the envelope of the RF pulse is a Sinc function. Using a Sinc function for the envelope of the RF pulse, it is possible to obtain the rectangular excitation profile except for the truncation error.

Imaging is performed according to the pulse sequence set in advance. Among the pulse sequences, there is an ultra-short echo time sequence (Ultra-short TE Sequence; hereinafter, referred to as a UTE sequence) to measure the signal of tissue having a short transverse relaxation time (T2) (PTL 1, NPL 1, and the like). In the UTE sequence, a half RF pulse having a waveform corresponding to the half waveform of a normal RF pulse (full RF pulse) is used as the envelope of the RF pulse. In addition, this half RF pulse is irradiated together with a slice gradient magnetic field with an inverted polarity, two excitations are performed, and echo signals are measured twice according to the excitation and are added. Hereinafter, a slice gradient magnetic field applied with its polarity as a positive polarity is called a positive polarity slice gradient magnetic field, a slice gradient magnetic field applied with its polarity as a negative polarity is called a negative polarity slice gradient magnetic field, an echo signal acquired when the positive polarity slice gradient magnetic field is applied is called positive polarity data, and an echo signal acquired when the negative polarity slice gradient magnetic field is applied is called negative polarity data.

Side lobe in the excitation profile based on the half RF pulse is larger than that in the excitation profile based on the full RE pulse. However, since the excitation profiles of the positive polarity data and the negative polarity data have phase distributions that are 180 [deg] inverted with respect to each other in their side lobe portions, the side lobe signals are canceled out by adding the positive polarity data and the negative polarity data. Accordingly, it is possible to obtain the excitation profile equivalent to the excitation profile based on the full RE pulse.

CITATION LIST

Patent Literature

[PTL 1] U.S. Pat. No. 5,025,216

Non Patent Literature

[NPL 1] P. D. Gatehouse, G. M. Bydder, Magnetic resonance imaging of short T2 components in issue, Clinical Radiology, 58(1), 1-19 (2003)

[NPL 2] Peter Latta et al., Simple phase method for measurement of magnetic field gradient waveforms, MAGNETIC RESONANCE IMAGING 25, 1272-1276 (2007)

SUMMARY OF INVENTION

Technical Problem

As described above, in the UTE sequence, side lobe signals of the excitation profiles are canceled out by adding the positive polarity data and the negative polarity data. In practice, however, the excitation profiles of the positive polarity data and the negative polarity data do not have phase distributions that are 180 [deg] inverted with respect to each other in their side lobe portions in many cases. In addition, a position shift may occur between the intensity distribution of the positive polarity data and the intensity distribution of the negative polarity data. In such a case, the side lobe signals of the positive polarity data and the negative polarity data are not canceled out. For this reason, signals from positions other than the designated slice position are mixed into a reconstructed image and artifacts are caused. Accordingly, it is not possible obtain a good image.

The present invention has been made in view of the above situation, and it is an object of the present invention to provide a high-quality image in the UTE sequence.

Solution to Problem

In the present invention, a good excitation profile is realized in the UTE sequence by adjusting the refocusing pulse of the slice gradient magnetic field so that the excitation profiles of positive polarity data and negative polarity data obtained by application of the half RF pulse have phase distributions that are 180 [deg] inverted with respect to each other in their side lobe portions.

Advantageous Effects of Invention

According to the present invention, in the UTE sequence, a high-quality image can be obtained regardless of the number of slices.

BRIEF DESCRIPTION OF DRAWINGS

FIG. 7($a$) is an explanatory view for explaining an excitation position shift when an offset occurs in the positive polarity slice gradient magnetic field, and FIG. 7($b$) is an explanatory view for explaining an excitation position shift when an offset occurs in the negative polarity slice gradient magnetic field.

FIGS. 9($a$) and 9($b$) are explanatory views for explaining measurement results of the positive polarity slice gradient magnetic field waveform and the negative polarity slice gradient magnetic field waveform in the first embodiment.

FIG. 16($a$) is an explanatory view for explaining the phase distribution after calculating a phase difference between positive polarity data and negative polarity data in the second embodiment, and FIG. 16($b$) is an explanatory view for explaining the phase distribution after performing phase unwrapping processing on the data shown in FIG. 6($a$).

FIGS. 19($a$) to 19($d$) are explanatory views for explaining the improvement effect of an image when a correction value is used in the second embodiment.

DESCRIPTION OF EMBODIMENTS

First Embodiment

Figure 1:
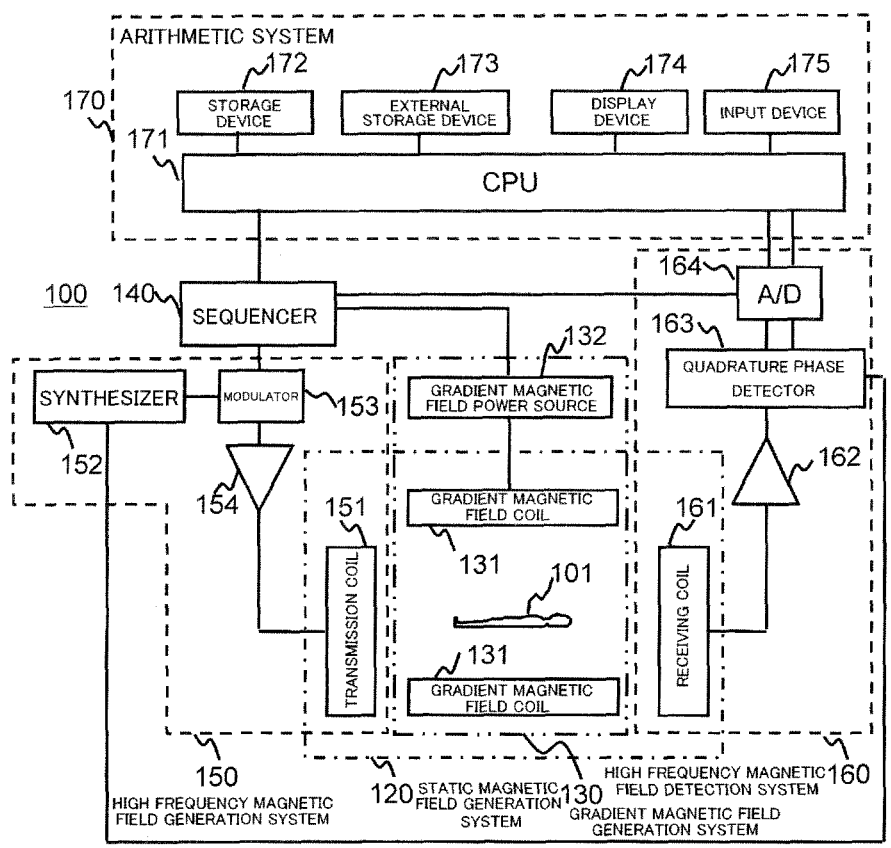
FIG. 1 is a block diagram of an MRI apparatus of a first embodiment.

A first embodiment to which the present invention is applied will be described with reference to the drawings. In addition, in all diagrams for explaining the embodiments of the invention, the same reference numerals are given to components having the same functions, and repeated explanation thereof will be omitted.

First, the outline of an MRI apparatus 100 of the present embodiment will be described with reference to FIG. 1. FIG. 1 is a block diagram showing the overall configuration of an MRI apparatus 100 of the present embodiment. The MRI apparatus 100 of the present embodiment is to obtain a tomographic image of an object using an NMR phenomenon, and includes a static magnetic field generation system 120, a gradient magnetic field generation system 130, a sequencer 140, a high frequency magnetic field generation system 150, a high frequency magnetic field detection system 160, and an arithmetic system 170.

The static magnetic field generation system 120 generates a uniform static magnetic field in space around an object 101 in a direction perpendicular to the body axis in the case of a perpendicular magnetic field method and in the body axis direction in the case of a horizontal magnetic field method. A permanent magnet type, normal conduction type, or superconducting type static magnetic field generator is disposed around the object 101.

The gradient magnetic field generation system 130 includes gradient magnetic field coils 131 wound in three axial directions of X, Y, and Z, which are the coordinate system (stationary coordinate system) of the MRI apparatus 100, and a gradient magnetic field power source 132 for driving each of the gradient magnetic field coils 131, and applies gradient magnetic fields Gxin, Gyin, and Gzin in the three axial directions of X, Y, and Z by driving the gradient magnetic field power source 132 of each coil according to an instruction from the sequencer 140, which will be described later. At the time of imaging, a slice-direction gradient magnetic field pulse (Gs) is applied in a direction perpendicular to a slice plane (imaging cross-section) so that a slice plane is set for the object 101, and a phase-encoding-direction gradient magnetic field pulse (Gp) and a frequency-encoding-direction gradient magnetic field pulse (Gf) are applied in the two remaining directions, which are perpendicular to the slice plane and are also perpendicular to each other, so that the position information in each direction is encoded in the NMR signal (echo signal).

The high frequency magnetic field generation system 150 emits an RF pulse to the object 101 in order to cause nuclear magnetic resonance in the nuclear spins of atoms that form the body tissue of the object 101, and includes a high frequency oscillator (synthesizer) 152, a modulator 153, a high frequency amplifier 154, and a transmission-side high frequency coil (transmission coil) 151. The high frequency pulse output from the synthesizer 152 is amplitude-modulated by the modulator 153 at a timing according to the instruction from the sequencer 140, and the amplitude-modulated high frequency pulse is amplified by the high frequency amplifier 154 and is supplied to the transmission coil 151 disposed adjacent to the object 101. As a result, an RF pulse is emitted to the object 101.

The high frequency magnetic field detection system 160 detects an echo signal (NMR signal) emitted by nuclear magnetic resonance of the nuclear spins of atoms, which form the body tissue of the object 101, and includes a receiving-side high frequency coil (receiving coil) 161, a signal amplifier 162, a quadrature phase detector 163, and an A/D converter 164. The echo signal of the response of the object 101 induced by the electromagnetic waves emitted from the transmission coil 151 is detected by the receiving coil 161 disposed adjacent to the object 101 and is amplified by the signal amplifier 162. Then, at a timing according to the instruction from the sequencer 140, the amplified signal is divided into signals of two systems perpendicular to each other by the quadrature phase detector 163, and each signal is converted into a digital amount by the A/D converter 164 and is transmitted to the arithmetic system 170.

The sequencer 140 is a control unit that applies a high frequency magnetic field pulse (hereinafter, referred to as an "RF pulse") and a gradient magnetic field pulse repeatedly according to a predetermined pulse sequence. The sequencer 140 operates under the control of the arithmetic system 170, and transmits various commands, which are required for data collection of the tomographic image of the object 101, to the gradient magnetic field generation system 130, the high frequency magnetic field generation system 150, and the high frequency magnetic field detection system 160. Since the gradient magnetic field generation system 130, the high frequency magnetic field generation system 150, and the high frequency magnetic field detection system 160 operate according to the command from the sequencer 140 and perform measurement, these are called a measurement system collectively.

The arithmetic system 170 performs various kinds of data processing, display and storage of processing results, and the like, and includes a CPU 171, a storage device 172, an external storage device 173, a display device 174, and an input device 175. For example, a tomographic image of the object 101 is reconstructed using the data from the high frequency magnetic field detection system 160. In addition, a control signal is transmitted to the sequencer 140 according to the imaging sequence. The reconstructed tomographic image is displayed on the display device 174 and is also recorded on the storage device 172 or the external storage device 73. The input device 175 is used when the operator inputs various kinds of control information of the MRI apparatus 100 or control information of processing performed in the arithmetic system 170, and includes a track ball, a mouse, and a keyboard. This input device 175 is disposed adjacent to the display device 174, so that the operator controls various kinds of processing of the MRI apparatus 100 interactively through the input device 175 while viewing the display device 174.

In addition, in FIG. 1, the transmission coil 151 and the gradient magnetic field coil 131 are provided in the static magnetic field space of the static magnetic field generation system 20, in which the object 101 is inserted, so as to face the object 101 in the case of a vertical magnetic field method and so as to surround the object 101 in the case of a horizontal magnetic field method. In addition, the receiving coil 161 is provided so as to face or surround the object 101.

Currently, nuclides imaged by an MRI apparatus, which are widely used clinically, are a hydrogen nucleus (proton) that is a main material of the object. The shapes or functions of the head, abdomen, limbs, and the like of the human body are imaged in a two-dimensional or three-dimensional manner by imaging the information regarding the spatial distribution of the proton density or the spatial distribution of the relaxation time of the excited state.

The imaging sequence by which the CPU 171 of the arithmetic system 170 gives a control signal to the sequencer 140 is determined by a pulse sequence, by which the application timing of the RF pulse and the gradient magnetic field pulse is determined, and a parameter specifying the application strength, application timing, and the like of the RF pulse and the gradient magnetic field pulse. The pulse sequence is set in advance, and is stored in the storage device 172. In addition, the parameter is calculated in the arithmetic system 170 on the basis of the imaging conditions set by the operator through the input device 175.

Figure 2:
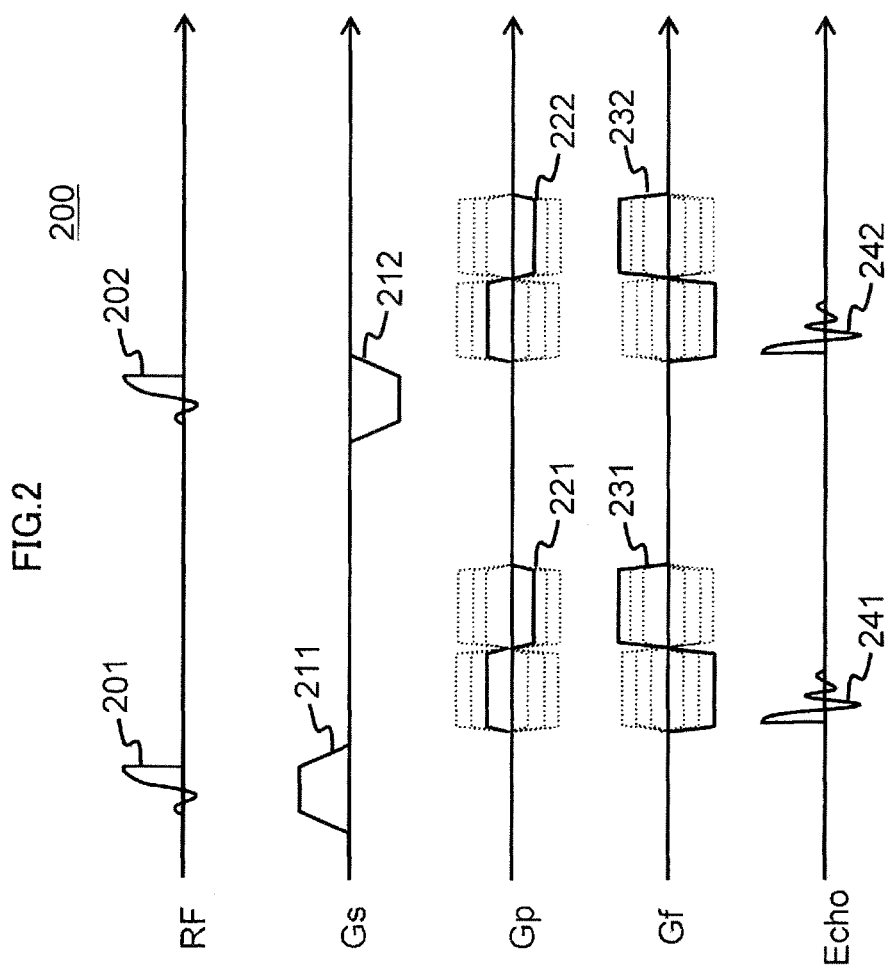
FIG. 2 is a pulse sequence diagram of a UTE sequence.

Here, a pulse sequence of the UTE sequence used in the present embodiment will be described. FIG. 2 shows a pulse sequence of a GTE sequence 200. In FIG. 2, all horizontal axes are time axes [s], vertical axes of RF and Echo are voltage amplitude [V], and vertical axes of Gs, Gp, and Gf are gradient magnetic field strength [T/m].

In the GTE sequence 200, half RF pulses 201 and 202 are applied together with slice gradient magnetic fields 211 and 212. In this case, slice gradient magnetic fields 211 and 212 are applied with opposite polarities. Hereinafter, a slice gradient magnetic field applied with a positive polarity is called a positive polarity slice gradient magnetic field, and a slice gradient magnetic field applied with a negative polarity is called a negative polarity slice gradient magnetic field. In addition, echo signals 241 and 242 are measured while applying phase encoding gradient magnetic fields 221 and 222 and readout encoding gradient magnetic fields 231 and 232. In addition, as described above, the echo signal 241 acquired by applying the positive polarity slice gradient magnetic field 211 is called positive polarity data, and the echo signal 242 acquired by applying the negative polarity slice gradient magnetic field 212 is called negative polarity data.

In addition, the arithmetic system 170 adds the measured echo signals 241 and 242 and then reconstructs an image. As described above, although the excitation profile of the half RF pulse has a larger side lobe than the excitation profile of the full RF pulse, it is possible to obtain the excitation profile equivalent to the full RF pulse by addition.

Figure 3:
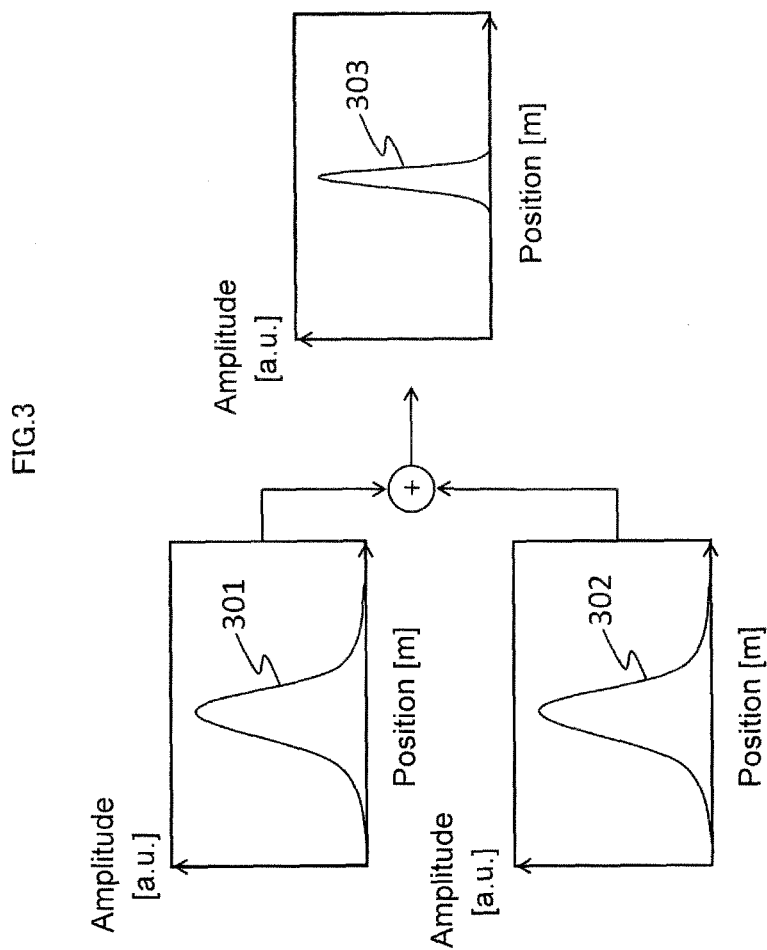
FIG. 3 is an excitation profile (intensity distribution) of the half RF pulse, and is an explanatory view for explaining that the side lobe in the excitation profile of the half RF pulse is reduced by adding positive polarity data and negative polarity data.

The reason why the side lobe of the excitation profile of the half RF pulse can be suppressed by addition will be described with reference to FIGS. 3 and 4. FIG. 3 shows excitation profiles 301 and 302 by the half RF pulses 201 and 202 and an excitation profile 303 of data, which is obtained by adding positive polarity data and negative polarity data obtained from the half RF pulses 201 and 202, of the UTE sequence 200. In FIG. 3, the horizontal axis indicates a position (Position [m]), and the vertical axis indicates an amplitude (Amplitude [a. u.]).

The excitation profile 303 equivalent to the full RF pulse can be obtained by adding the echo signals. The reason can be explained from the phase distribution of the excitation profile by the half RF pulse.

Figure 4:
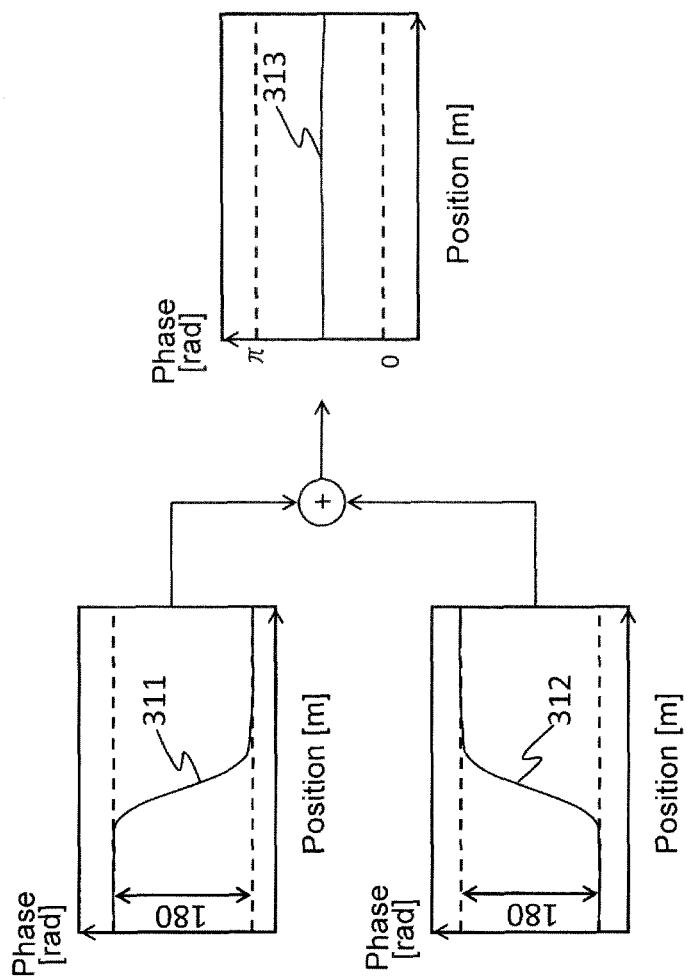
FIG. 4 is an excitation profile (phase distribution) of the half RF pulse, and is an explanatory view for explaining that the excitation profiles of positive polarity data and negative polarity data have phase distributions that are 180 [deg] inverted with respect to each other in their side lobe portions.

FIG. 4 shows phase distributions 311 and 312 of the excitation profiles by the half RF pulses 201 and 202. In FIG. 4, the horizontal axis indicates a position (Position [m]), and the vertical axis indicates a phase (Phase [deg]).

As shown in FIG. 4, the phase distribution 311 of the excitation profile 301 obtained by the positive polarity slice gradient magnetic field 211 and the phase distribution 312 of the excitation profile 302 obtained by the negative polarity slice gradient magnetic field 212 are in the relationship of 180 [deg] inversion in the side lobe portions. Therefore, phase distribution 313 in which side lobe signals are canceled out is obtained by adding the data (positive polarity data and negative polarity data) obtained by both slice gradient magnetic fields.

However, the phase distribution of the excitation profile of the positive polarity data and the phase distribution of the excitation profile of the negative polarity data are not in the relationship of 180 [deg] inversion in practice unlike those described above. In addition, a position shift occurs between the intensity distribution of the positive polarity data and the intensity distribution of the negative polarity data.

The reason why the phase distribution of the positive polarity data and the phase distribution of the negative polarity data are not in the relationship of 180 [deg] inversion is an eddy current generated by the slice gradient magnetic field and the relaxation of the half RF pulses 201 and 202 during irradiation.

Figure 5:
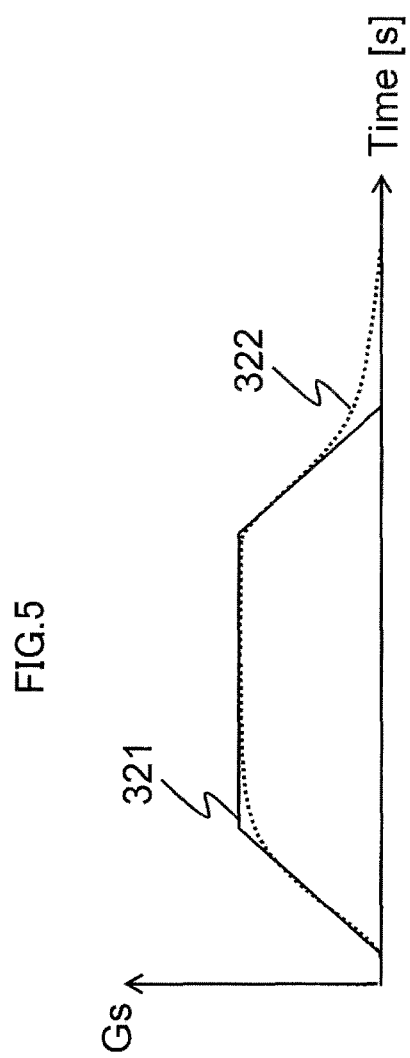
FIG. 5 is a diagram for explaining the distortion of an output gradient magnetic field waveform due to a magnetic field generated by an eddy current.

When an eddy current is generated in the slice gradient magnetic fields 211 and 212, waveforms of the slice gradient magnetic fields 211 and 212 are deformed. As a result, the phase of nuclear spins is dispersed after the application of the half RF pulses 201 and 202, and the phase distribution of the excitation profile is changed. FIG. 5 is a conceptual diagram showing the state of a waveform 322 of a slice gradient magnetic field, which has been changed due to the generation of an eddy current, with respect to a waveform 321 of a slice gradient magnetic field designated by the imaging parameter.

Figure 6:
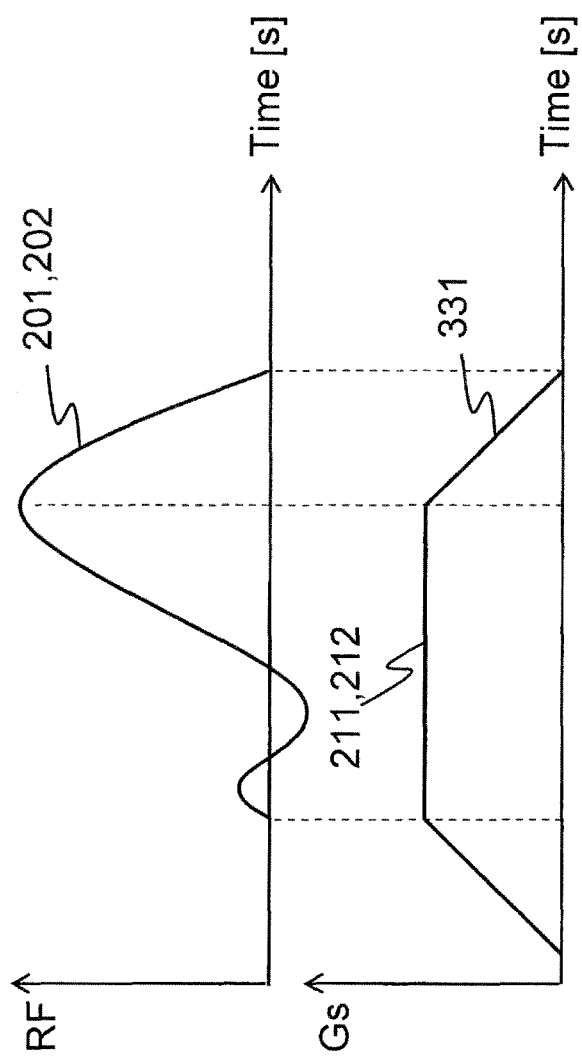
FIG. 6 is an explanatory view for explaining the application timing of the RF pulse and the slice gradient magnetic field when a down portion of the slice gradient magnetic field is also used to irradiate the half RF pulse.

In addition, the phase dispersion of nuclear spins is also caused by the relaxation of the half RF pulses 201 and 202 during irradiation, and the phase distribution of the excitation profile is changed. In particular, as shown in FIG. 6, in the case of a pulse sequence in which a down portion 331 of the slice gradient magnetic fields 211 and 213 is also used to irradiate the half RF pulses 201 and 202, the influence of relaxation becomes noticeable. This is because the irradiation intensity of the half RF pulses 201 and 202 is reduced according to the strength of the slice gradient magnetic fields 211 and 212 and accordingly the flip angle of nuclear spins is reduced in a portion where the irradiation intensity has been reduced and the irradiation time is also increased.

On the other hand, the reason why a position shift occurs between the intensity distribution of the positive polarity data and the intensity distribution of the negative polarity data is an offset component of the slice gradient magnetic fields 211 and 212. When an offset occurs in the slice gradient magnetic fields 211 and 212, the excitation position shifts in proportion to the offset. Since the shift when the slice gradient magnetic field has a positive polarity and the shift when the slice gradient magnetic field has a negative polarity occur in opposite directions, the intensity distributions of both slice gradient magnetic fields are not equal. Accordingly, the width of the main lobe is increased and a side lobe signal remains when adding both slice gradient magnetic fields.

FIGS. 7(a) and 7(b) are diagrams for explaining a state where an excitation position 342 shifts from a position 341, at which excitation is needed, in proportion to an offset 343 when an offset occurs in the slice gradient magnetic field. FIG. 7(a) shows a case where the slice gradient magnetic field has a positive polarity (positive polarity slice gradient magnetic field 211). In addition, FIG. 7(b) shows a case where the slice gradient magnetic field has a negative polarity (negative polarity slice gradient magnetic field 212). As shown in these diagrams, the actual excitation positions 342 in cases of the positive polarity slice gradient magnetic field 211 and the negative polarity slice gradient magnetic field 212 are shifted in opposite directions. Accordingly, since the intensity distributions of both slice gradient magnetic fields 211 and 212 are not equal, the width of the main lobe is increased and a side lobe signal remains when adding both slice gradient magnetic fields 211 and 212.

In addition, the side lobe signal can be suppressed by applying a saturation pulse so as to be adjacent to the slice plane. However, in the case of measurement using a multi-slice method (pulse sequence of exciting a plurality of slices within the TR), it is not possible to apply a saturation pulse adjacent to each slice plane since a plurality of slices are continuously excited. Therefore, since a side lobe signal cannot be suppressed, a signal from a position other than the designated slice position is mixed in a reconstructed image. As a result, a good image is not obtained.

In the present embodiment, the waveforms of the slice gradient magnetic fields 211 and 212 are measured, a correction value is calculated from the result, and a pulse sequence and reconstruction processing are changed using the correction value. The processing of the arithmetic system 170 of the present embodiment is largely divided into two processes. The first process is pre-processing for calculating the correction value, which is used in the pulse sequence and the reconstruction processing, from the measurement result of the waveforms of the slice gradient magnetic fields 211 and 212. The correction values calculated in the pre-processing are the following three: 1) refocusing area of the slice gradient magnetic field (refocusing pulse application amount of the slice gradient magnetic fields 211 and 212), 2) irradiation frequencies of the half RF pulses 201 and 202, and 3) zero-order term (zero-order phase difference) of the phase difference between positive polarity data and negative polarity data. The second process is main measurement processing in which measurement is performed by changing the UTE sequence 200 reflecting the calculated refocusing pulse application amount and irradiation frequency in the UTE sequence 200 while performing reconstruction reflecting the zero-order phase difference.

Figure 8:
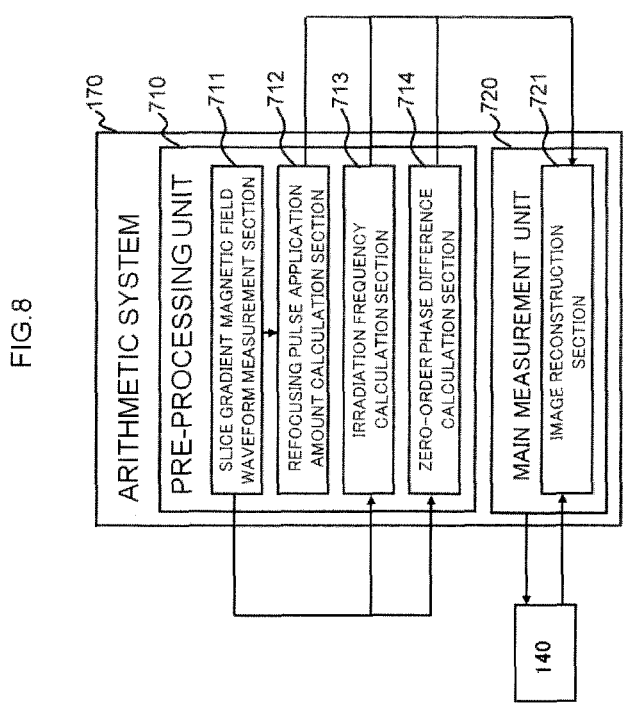
FIG. 8 is a functional block diagram of an arithmetic system of the first embodiment.

In order to realize these processes, the arithmetic system 170 of the present embodiment includes a pre-processing unit 710 and a main measurement unit 720 as shown in FIG. 8. In addition, the pre-processing unit 710 includes a slice gradient magnetic field waveform measurement section 711, a refocusing pulse application amount calculation section 712, an irradiation frequency calculation section 713, and a zero-order phase difference calculation section 714. The main measurement unit 720 includes an image reconstruction section 721.

Any function of the arithmetic system 170 is realized when the CPU 171 of the arithmetic system 170 loads a program stored in advance in the storage device 172 or the external storage device 173 to the memory and executes it. This is the same for all embodiments described below.

Hereinafter, details of processing of each section will be described. Here, a case of performing multi-slice imaging when the number of slices is N (N is a natural number) will be described as an example. In addition, imaging is not limited to the multi-slice imaging.

The slice gradient magnetic field waveform measurement section 711 measures a slice gradient magnetic field waveform, which is actually applied, at each slice position. The measurement is performed using a known technique. In the UTE sequence 200, when the slice gradient magnetic fields 211 and 212 are applied according to the imaging parameter, a slice gradient magnetic field waveform that is output is determined.

For example, when using the method disclosed in NPL 2, measurement is performed as follows. A slice gradient magnetic field whose waveform is to be measured is assumed to be a test gradient magnetic field. After exciting a predetermined thin slice, a sequence for acquiring a signal by applying the test gradient magnetic field according to the imaging parameter and a reference sequence for acquiring a signal without applying the test gradient magnetic field are performed, and a gradient magnetic field output waveform of the test gradient magnetic field (slice gradient magnetic field) is measured by an operation between the signals obtained by the two sequences.

In the present embodiment, each waveform of the positive polarity slice gradient magnetic field 211 and the negative polarity slice gradient magnetic field 212 is measured. The obtained positive polarity slice gradient magnetic field waveform is assumed to be Waveform_positive(x), and the obtained negative polarity slice gradient magnetic field waveform is assumed to be Waveform_negative(x). Here, x indicates a discrete point number showing the position in a slice direction.

FIG. 9(a) shows Waveform_positive(x) 411, and FIG. 9(b) shows Waveform_negative(x) 412. Here, a waveform when there is a gradient magnetic field offset GcOffset is shown. Here, RF_Start_Time is the application start time of each of the half RE pulses 201 and 202. In addition, RF_End_Time is the application end time of each of the half RF pulses 201 and 202. As shown in these diagrams, the shape of the slice gradient magnetic field that is actually applied is distorted from the rectangle, and is also applied after the end of half RF pulse application (RF_End_Time).

The refocusing pulse application amount calculation section 712 calculates, as a correction value, the refocusing pulse application amount of each of the positive polarity slice gradient magnetic field 211 and the negative polarity slice gradient magnetic field 212 at each slice position.

Figure 10:
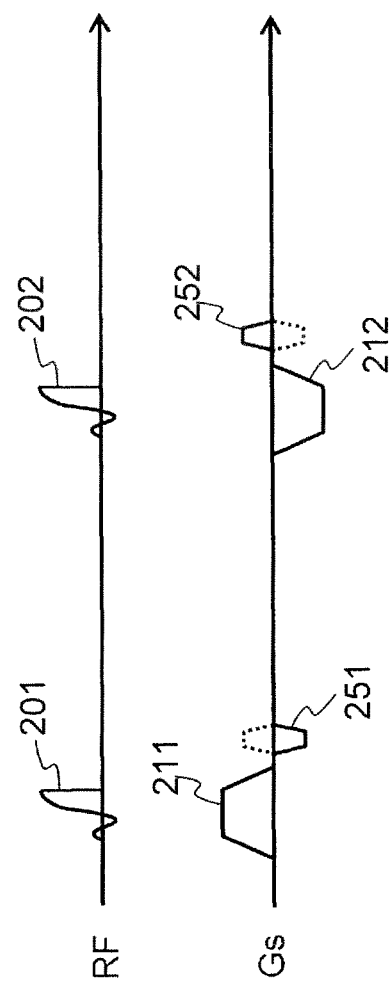
FIG. 10 is an explanatory view for explaining the application timing of the refocusing pulse of the slice gradient magnetic field pulse.

As shown in FIGS. 9(a) and 9(b), a gradient magnetic field generated due to the influence of an eddy current or the like is applied during the time (TE) until the acquisition of the echo signals 241 and 242 after irradiation of the half RF pulses 201 and 202. The refocusing pulses are area adjustment pulses applied in order to cancel out the gradient magnetic field application amounts (surplus application amounts of the slice gradient magnetic fields) during this period. As shown in FIG. 10, refocusing pulses 251 and 252 are applied immediately after the application of the slice gradient magnetic fields 211 and 212, respectively.

The refocusing pulse application amount calculation section 712 of the present embodiment calculates the surplus application amounts of the slice gradient magnetic fields 211 and 212 using the measured slice gradient magnetic field waveforms Waveform_positive(x) 411 and Waveform_negative(x) 412, and determines the application amount so as to cancel out the surplus application amounts.

Specifically, the refocusing pulse application amount calculation section 712 of the present embodiment calculates the application amount (area) of the refocusing pulse 251 using the following Expressions (1) and (2).

[Expression 1]

$$\text{Adjust\_Area\_251} = \sum_{x=RF\_End\_Time}^{RF\_End\_Time+TE} \text{Waveform\_positive}(x) \quad (1)$$

[Expression 2]

$$\text{Adjust\_Area\_252} = \sum_{x=RF\_End\_Time}^{RF\_End\_Time+TE} \text{Waveform\_negative}(x) \quad (2)$$

Here, Adjust_Area_251 is an area [s·T/m] of the refocusing pulse 251, Adjust_Area_252 is the area [s·T/m] of the refocusing pulse 252, RF_End_Time is the irradiation end time [s] of the half RF pulses 201 and 202, and TE is a time from the irradiation end time of the half RF pulses 201 and 202 to the acquisition of the echo signals 241 and 242.

The irradiation frequency calculation section 713 calculates the irradiation frequencies of the half RF pulses 201 and 202, which are irradiated at each slice position, as correction values. When there is an excitation position shift between the positive polarity slice gradient magnetic field 211 and the negative polarity slice gradient magnetic field 212, the irradiation frequency calculation section 713 of the present embodiment determines each irradiation frequency according to the obtained slice gradient magnetic field waveforms so that the position shift is eliminated. The excitation position shift is calculated on the basis of the measured strength of each of the slice gradient magnetic fields 211 and 212.

Specifically, the irradiation frequency calculation section 713 of the present embodiment calculates the irradiation frequency Frequency_Positive [Hz] of the half RF pulse 201, which is applied together with the positive polarity slice gradient magnetic field 211, and the irradiation frequency Frequency_Negative [Hz] of the half RF pulse 202, which is applied together with the positive polarity slice gradient magnetic field 212, according to the following Expressions (3) and (4) using the waveform Waveform_positive(x) of the determined slice gradient magnetic field 211 and the waveform Waveform_negative(x) of the determined slice gradient magnetic field 212.

[Expression 3]

$$\text{Frequency\_Positive} = \gamma \cdot \text{Offcenter} \cdot Gc\text{Amp1} + \gamma \cdot Gc\text{Base} \quad (3)$$

[Expression 4]

$$\text{Frequency\_Negative} = \gamma \cdot \text{Offcenter} \cdot Gc\text{Amp2} + \gamma \cdot Gc\text{Base} \quad (4)$$

Here, $\gamma$ is a gyromagnetic ratio [Hz/T], GcAmp1 is the measured strength [T/m] of the positive polarity slice gradient magnetic field 211 (strength of a plateau portion of the measured waveform 411 of the positive polarity slice gradient magnetic field 211 shown in FIG. 9(a)), GcAmp2 is the measured strength [T/m] of the negative polarity slice gradient magnetic field 212 (strength of a plateau portion of the measured waveform 412 of the negative polarity slice gradient magnetic field 212 shown in FIG. 9(b)), Offcenter is a distance [m] from the magnetic field center to the designated slice position, and GcBase is a static magnetic field strength [T].

The zero-order phase difference calculation section 714 calculates, as a correction value, a value (zero-order phase difference) of the zero-order term of the difference between the phase of the acquired positive polarity data and the phase of the acquired negative polarity data at each slice position. Using the measured waveform of the positive polarity slice gradient magnetic field 211 and the measured waveform of the negative polarity slice gradient magnetic field 212, the zero-order phase difference calculation section 714 of the present embodiment calculates the zero-order phase difference using the following Expression (5).

[Expression 5]

$$ZerothOrderPhase = 360 \times \sum_{x=RF\_Start\_Time}^{RF\_End\_Time} (\gamma \cdot Offcenter \cdot \\ (\text{Waveform\_positive}(x) - \text{Waveform\_negative}(x)) \cdot \Delta x) \quad (5)$$

Here, ZerothOrderPhase is a zero-order phase difference [deg], RF_Start_Time is the irradiation start time [s] of each of the half RF pulses 201 and 202, Offcenter is a distance [m] from the magnetic field center to the designated slice position, and Δx is a sampling interval [s] of Waveform_positive( ) and Waveform_negative( ).

In addition, Expression (5) is an expression for calculating the phase shift of the negative polarity data with respect to the positive polarity data.

In Expression (5), the phase shift of the positive polarity data with respect to the negative polarity data may be calculated by replacing Waveform_positive(x) and Waveform_negative (y) with each other.

The main measurement unit 720 of the present embodiment sets the refocusing pulse application amount and the irradiation frequency, which have been calculated as correction values by the refocusing pulse application amount calculation section 712 and the irradiation frequency calculation section 713, in the UTE sequence 200, and performs main measurement.

The image reconstruction section 721 adds the positive polarity data and the negative polarity data obtained by the main measurement, and reconstructs an image from data (polarity addition data) obtained by the addition using a known method, such as a Fourier transform. In this case, in the present embodiment, the phase difference between the positive polarity data and the negative polarity data is corrected using the zero-order phase difference before the addition.

Here, a case where the phase shift of the negative polarity data with respect to the positive polarity data is calculated as the zero-order phase difference (case of the above Expression (5)) will be described as an example. In this case, the zero-order phase difference calculated by Expression (5) is added to the negative polarity data according to the following Expressions (6) and (7).

[Expression 6]

$$\text{Main\_negative}'(real, x) = \\ \text{Main\_negative}(real, x) \cdot \cos(ZerothOrderPhase) + \\ \text{Main\_negative}(imgn, x) \cdot \sin(ZerothOrderPhase) \quad (6)$$

[Expression 7]

$$\text{Main\_negative}'(imgn, x) = \\ \text{Main\_negative}(imgn, x) \cdot \cos(ZerothOrderPhase) - \\ \text{Main\_negative}(real, x) \cdot \sin(ZerothOrderPhase) \quad (7)$$

Here, Main_negative(real,) and Main_negative(imagn,) are the real part and imaginary part of negative polarity data before zero-order phase addition, Main_negative'(real,) and Main_negative'(imagn,) are the real part and imaginary part of negative polarity data after zero-order phase addition, and ZerothOrderPhase is a zero-order phase difference [deg] calculated by Expression (5).

The addition of the negative polarity data and the positive polarity data after zero-order phase addition is based on the following Expressions (8) and (9).

[Expression 8]

$$\text{Main\_composed}(real,x) = \text{Main\_positive}(real,x) + \\ \text{Main\_negative}'(real,x) \quad (8)$$

[Expression 9]

$$\text{Main\_composed}(imgn,x) = \text{Main\_positive}(imgn,x) + \\ \text{Main\_negative}'(imgn,x) \quad (9)$$

Here, Main_positive(real,) and Main_positive(imagn,) are the real part and imaginary part of positive polarity data before zero-order phase addition, Main_composed(real,) and Main_composed(imagn,) are the real part and imaginary part of polarity-added data.

In addition, when a zero-order phase difference is calculated as the phase shift of the positive polarity data with respect to the negative polarity data, the zero-order phase difference is added to the positive polarity data side using the method described above, and then the positive polarity data and the negative polarity data after the addition are added.

Figure 11:
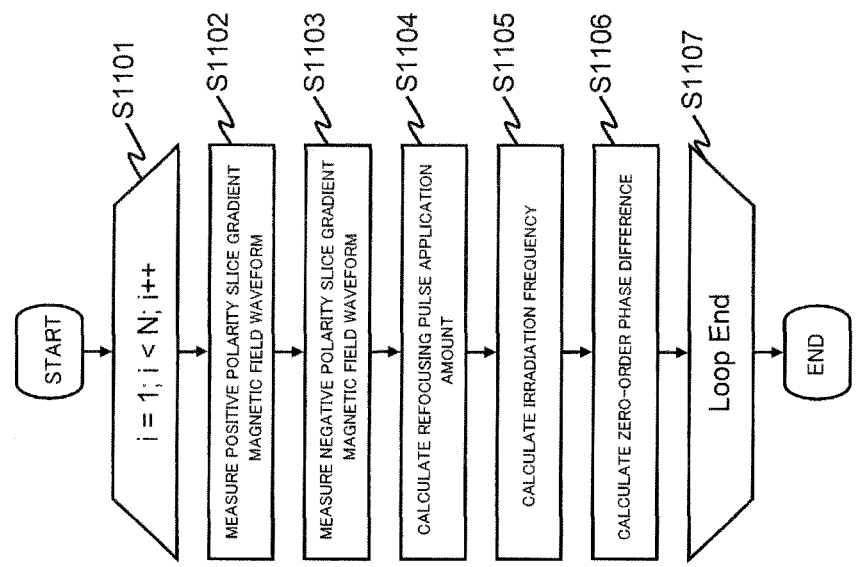
FIG. 11 is a flow chart of pre-processing of the first embodiment.

Next, the flow of each process of the arithmetic system 170 of the present embodiment will be described. First, the flow of the pre-processing by the pre-processing unit 710 will be described. FIG. 11 is a process flow showing the flow of pre-processing of the present embodiment. As described above, the pre-processing unit 710 performs pre-processing for calculating a correction value for each slice. Here, the total number of slices is set to N.

The pre-processing unit 710 repeats the process of steps S1102 to S1106 by the iterative process (steps S1101 and S1107). The number of repetitions is the number of slices (here, N) designated as the imaging conditions of the main measurement. Here, the number of slices to be processed during the repetitive processing is expressed as i.

First, the slice gradient magnetic field waveform measurement section 711 measures the waveform of the positive polarity slice gradient magnetic field 211 at the i-th slice position (step S1102), and then measures the waveform of the negative polarity slice gradient magnetic field 212 (step S1103). In addition, any of the waveforms of the slice gradient magnetic fields 211 and 212 may be measured first.

Then, the refocusing pulse application amount calculation section 712 calculates the application amounts of the refocusing pulses 251 and 252 with respect to each slice gradient magnetic field at the i-th slice position according to the above Expressions (1) and (2) using the measured waveform of the positive polarity slice gradient magnetic field 211 and the measured waveform of the negative polarity slice gradient magnetic field 212, respectively (step S1104).

Then, the irradiation frequency calculation section 713 calculates the irradiation frequencies of the half RF pulses 201 and 202 at the i-th slice position according to the above Expressions (3) and (4) using the measured waveform of the positive polarity slice gradient magnetic field 211 and the measured waveform of the negative polarity slice gradient magnetic field 212, respectively (step S1105).

Then, the zero-order phase determination section calculates a zero-order phase difference between the positive polarity data and the negative polarity data at the i-th slice position according to the above Expression (5) using the measured waveform of the positive polarity slice gradient magnetic field 211 and the measured waveform of the negative polarity slice gradient magnetic field 212 (step S1106).

The arithmetic system 170 of the present embodiment performs pre-processing as described above, thereby calculating the correction values of the irradiation frequencies of the half RF pulses 201 and 202, the correction values of the application amounts of the refocusing pulses 251 and 252, and the correction value of the zero-order phase difference.

In addition, any processing of S1103, S1104, and S1105 may be performed first after step S1102.

Figure 12:
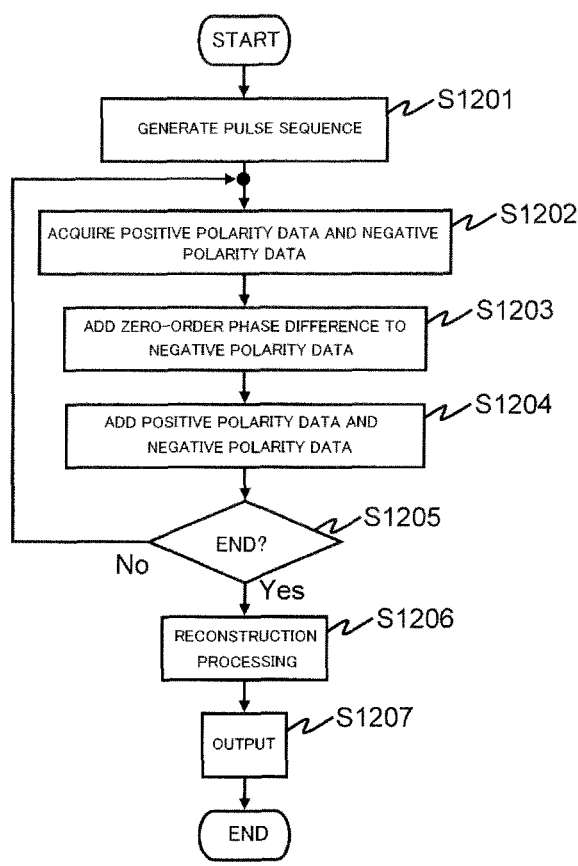
FIG. 12 is a flow chart of main measurement processing of the first embodiment.

Next, main measurement processing of the main measurement unit 720 of the present embodiment will be described. FIG. 12 is a process flow of the main measurement processing of the present embodiment.

First, the main measurement unit 720 generates a pulse sequence, which is used in the main measurement, using the set imaging parameter and the correction values determined in the pre-processing (step S1201). Here, the irradiation frequency and the refocusing pulse application amount determined for each slice are reflected in the UTE sequence 200 shown in FIG. 2.

Then, the main measurement unit 720 gives an instruction to the sequencer 140 according to the generated UTE sequence 200 and performs measurement to acquire positive polarity data and negative polarity data (step S1202).

The image reconstruction section 721 adds the zero-order phase difference calculated by pre-processing to the negative polarity data (step S1203). Then, the image reconstruction section 721 adds the positive polarity data and the negative polarity data after addition (step S1204), thereby obtaining polarity-added data.

The main measurement unit 720 repeats the processing of steps S1202 to S1204 until determination of the end of measurement is made (step S1205). Here, the determination of the end of measurement is defined in advance. For example, when the number of acquired echoes satisfies the conditions of a specified number or when an instruction to interrupt processing is received, determination of the end of measurement is made. When determination of the end of measurement is made, the image reconstruction section 721 reconstructs the image from the polarity-added data (step S1206), and outputs the result to the display device 174, the storage device 172, the external storage device 173, and the like (step S1207).

In addition, although the number of slices N set in the imaging conditions is set as the number of repetitions in the above explanation of the main measurement processing, the number of repetitions is not limited thereto. For example, it is possible to designate all slice positions where imaging is possible of the MRI apparatus 100 and repeat imaging by the number of positions.

In addition, irradiation frequency calculation processing is performed when there is a shift between the excitation position of the positive polarity data and the excitation position of the negative polarity data. In the case of an MRI apparatus in which an excitation position shift is difficult to occur, the above-described calculation of the irradiation frequency may not be performed. In this case, the irradiation frequency calculation section 713 may not be provided. The main measurement unit 720 sets the irradiation frequency set by the imaging parameter or the irradiation frequency calculated by the known technique in the UTE sequence 200.

In addition, when it is known that the zero-order phase difference does not significantly affect the image quality, it is not necessary to calculate the zero-order phase difference. In this case, the zero-order phase difference calculation section 714 may not be provided. When the zero-order phase difference is not calculated, for example, 0 [deg] may be set as a phase difference or one of the negative polarity data and the positive polarity data before addition by the image reconstruction section 721 may not be corrected.

As described above, according to the present embodiment, there is provided a magnetic resonance imaging apparatus including: a static magnetic field generation system 120; a measurement system including a gradient magnetic field generation system 130, a high frequency magnetic field generation system 150, and a high frequency magnetic field detection system 160; and an arithmetic system 170 that controls an operation of the measurement system according to a pulse sequence to measure a nuclear magnetic resonance signal and performs calculation using data obtained from the nuclear magnetic resonance signal. The pulse sequence is an ultra-short echo time sequence to obtain each echo signal by performing two slice selection excitations by inverting a polarity of a slice gradient magnetic field, which is applied together with a half RF pulse, between a positive polarity and a negative polarity. The arithmetic system 170 includes a pre-processing unit 710 that calculates a correction value used in the measurement and the calculation and a main measurement unit 720 that sets the correction value calculated by the pre-processing unit 710 in the pulse sequence and performs main measurement by controlling the measurement system according to the pulse sequence after the setting so that an image is reconstructed. The pre-processing unit 710 includes a refocusing pulse application amount calculation section 712 that calculates an application amount of a refocusing pulse of each slice gradient magnetic field as the correction value. The main measurement unit 720 includes an image reconstruction section 721 that adds positive polarity data, which is an echo signal obtained when the slice gradient magnetic field having a positive polarity is applied, and negative polarity data, which is an echo signal obtained when the slice gradient magnetic field having a negative polarity is applied, in the main measurement and reconstructs an image using polarity-added data after the addition. The refocusing pulse application amount calculation section 712 calculates the application amount of each refocusing pulse so as to reduce a side lobe signal of an excitation profile after adding the positive polarity data and the negative polarity data.

In addition, the pre-processing unit 710 includes a slice gradient magnetic field waveform measurement section 711 that measures a slice gradient magnetic field waveform of the pulse sequence, and the refocusing pulse application amount calculation section 712 calculates the application amount of each refocusing pulse using the measured slice gradient magnetic field waveform.

That is, according to the present embodiment, in imaging based on the UTE sequence to add positive polarity data and negative polarity data using a half RF pulse, the application amount of the refocusing pulse used in the main measurement is determined on the basis of measurement data of the slice gradient magnetic field waveform that is actually applied. Therefore, according to the present embodiment, it is possible to eliminate the influence of the slice gradient magnetic field, which is unnecessarily applied, by the application of the appropriate refocusing pulse even when the excitation profiles of the positive polarity data and the negative polarity data do not have phases, which are 180 [deg] inverted with respect to each other, unlike the theory due to influences, such as the offset and distortion of the slice gradient magnetic field pulse due to an eddy current.

In this manner, the phase distributions of the excitation profiles of the positive polarity data and the negative polarity data can be brought close to a state where the phases are 180 [deg] inverted with respect to each other. Accordingly, since the excitation profile of polarity-added data can be made as a good excitation profile that is steep and has a small amount of side lobe, it is possible to prevent the mixing of signals from positions other than the designated slice position in a reconstructed image. Therefore, it is possible to obtain a high-quality reconstructed image in which artifacts are suppressed.

In addition, the pre-processing unit 710 may further include an irradiation frequency calculation section 713 that calculates the irradiation frequency of the half RF pulse as the correction value. In this case, the irradiation frequency calculation section 713 calculates the irradiation frequency so as to eliminate a position shift between the two slice selection excitation positions, and the position shift is calculated using the strength of the slice gradient magnetic field obtained from the measured slice gradient magnetic field waveform.

In general, when a position shift occurs between the intensity distributions of positive polarity data and negative polarity data, the width of the main lobe of the excitation profile is increased and a side lobe signal remains. However, according to the present embodiment, the irradiation frequency of the half RF pulse is determined on the basis of the measurement data of the slice gradient magnetic field waveform that is actually applied. For this reason, it is possible to suppress a shift of the excitation position. Therefore, it is possible to obtain a steep excitation profile with a small amount of side lobe signal. As a result, it is possible to obtain an image with higher image quality.

In addition, the pre-processing unit 710 may further include a zero-order phase difference calculation section 714 that calculates a zero-order phase difference, which is a zero-order term of a phase difference between the positive polarity data and the negative polarity data, as the correction value. In this case, the image reconstruction section 721 corrects the phase difference between the positive polarity data and the negative polarity data using the zero-order phase difference before the addition. The zero-order phase difference calculation section 714 calculates the zero-order phase difference using a difference between a slice gradient magnetic field waveform when the polarity is a positive polarity and a slice gradient magnetic field waveform when the polarity is a negative polarity.

Therefore, according to the present embodiment, the phase difference between the positive polarity data and the negative polarity data is calculated on the basis of the measurement data of the slice gradient magnetic field waveform that is actually applied. In addition, these pieces of data are corrected using the calculated phase difference. Therefore, since a phase difference can be accurately corrected, it is possible to obtain a better excitation profile. As a result, it is possible to obtain an image with higher image quality.

In addition, in the above embodiment, the case where pre-processing is performed for each slice has been described as an example. This is because the output characteristics of the gradient magnetic field differ depending on the slice position and accordingly each calculated value (irradiation frequency, application amount, and zero-order phase difference) changes according to the position. However, the present invention is not limited thereto. For example, when there is no significant change in the output characteristics of the gradient magnetic field according to the slice position, each value described above may be calculated with only a representative slice position as a processing target. By adopting such a configuration, it is possible to increase the processing speed.

In addition, according to the present embodiment, also in a multi-slice method, it is possible to effectively suppress the side lobe signal. That is, in the multi-slice method, since a plurality of slices are continuously excited within the TR, it is not possible to suppress the side lobe signal by applying a saturation pulse so as to be adjacent to each slice plane. Therefore, when the saturation pulse is used, the saturation pulse is applied outside the entire region to be imaged. Since a signal in a range from the slice plane to the saturation pulse application position is not suppressed by the saturation pulse, signals from positions other than the designated slice position are mixed into the reconstructed image when a side lobe signal is present. In the present embodiment, however, the side lobe signal is reduced by improving the shape of the excitation profile itself. Therefore, even in the multi-slice method, the side lobe signal can be sufficiently reduced. As a result, it is possible to obtain a high-quality image as in other measurements.

In addition, the pre-processing may be performed immediately before the main measurement, or may be performed at the time of installation of the apparatus. When the pre-processing is performed at the time of installation work of the apparatus, the obtained refocusing pulse application amount, irradiation frequency, and zero-order phase difference may be stored in the storage device 172 or the like so as to match the slice gradient magnetic field whose waveform has been measured.

Second Embodiment

Next, a second embodiment to which the present invention is applied will be described. In the present embodiment, the excitation position shift amount is calculated from the excitation profiles of positive polarity data and negative polarity data and a zero-order phase difference and a first-order phase difference are calculated from the phase distribution of both pieces of data, thereby obtaining each correction value. This correction value is reflected in the pulse sequence and reconstruction processing.

The MRI apparatus 100 of the present embodiment has basically the same configuration as in the first embodiment. In addition, the pulse sequence used in imaging is also the UTE sequence 200 as the first embodiment. However, since a method of calculating the correction value is different, the configuration of the pre-processing unit 710 is different. Hereinafter, the present embodiment will be described focusing on the different configuration from the first embodiment.

Figure 13:
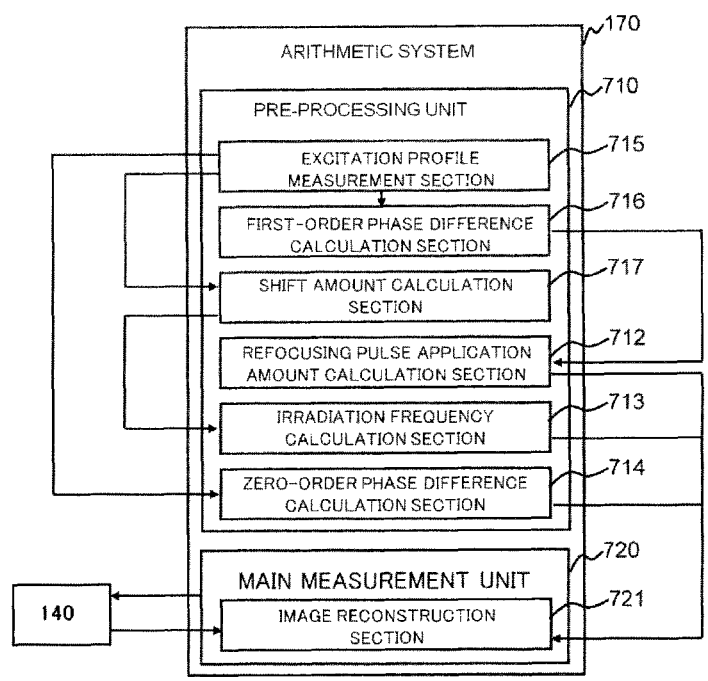
FIG. 13 is a functional block diagram of an arithmetic system of a second embodiment.

As shown in FIG. 13, the pre-processing unit 710 of the present embodiment includes an excitation profile measurement section 715, a first-order phase difference calculation section 716, and a shift amount calculation section 717 in addition to the refocusing pulse application amount calculation section 712, the irradiation frequency calculation section 713, and the zero-order phase difference calculation section 714.

In addition, similar to the first embodiment, the arithmetic system 170 includes the pre-processing unit 710 and the main measurement unit 720, and the main measurement unit 720 includes the image reconstruction section 721.

The pre-processing unit 710 of the first embodiment calculates each of the above-described correction values on the basis of the measured waveforms of the slice gradient magnetic fields 211 and 212. On the other hand, the pre-processing unit 710 of the present embodiment calculates a correction value from the profile (intensity distribution and phase distribution) of excitation by the half RF pulse that is performed according to the set imaging parameter. That is, the excitation position shift amount and the zero-order and first-order phase differences of positive polarity data and negative polarity data that minimize aside lobe are calculated from the excitation profile.

Figure 14:
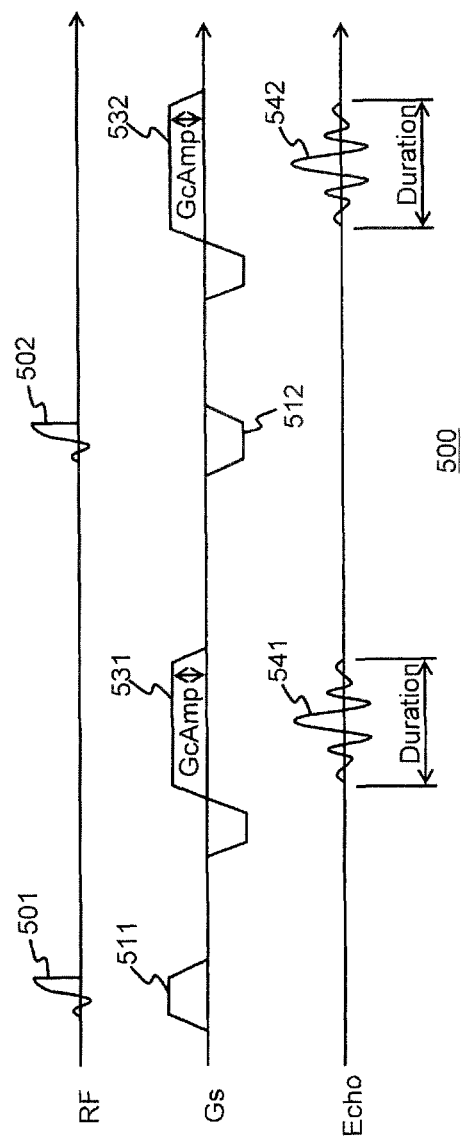
FIG. 14 is a pulse sequence diagram of an excitation profile measurement sequence of the second embodiment.

The excitation profile measurement section 715 measures an excitation profile for each slice and each polarity of the slice gradient magnetic field. A pulse sequence (excitation profile measurement sequence) 500 shown in FIG. 14 is used in excitation profile measurement.

In the excitation profile measurement sequence 500, half RF pulses 501 and 502, a positive polarity slice gradient magnetic field 511 and a negative polarity slice gradient magnetic field 512 that are applied together with the half RF pulses 501 and 502, and readout encoding gradient magnetic fields 531 and 532 that are applied in a slice direction at the time of acquisition of echo signals 541 and 542 are provided.

The excitation profile measurement section 715 executes the excitation profile measurement sequence 500 using an imaging parameter for the main measurement. That is, the half RF pulses 501 and 502, the positive polarity slice gradient magnetic field 511, and the negative polarity slice gradient magnetic field 512 are made to match those used at the time of main measurement. In addition, a Fourier transform of each of the obtained echo signals 541 and 542 is performed to obtain the excitation profile at the time of positive polarity and the excitation profile at the time of negative polarity.

In this case, each of the obtained excitation profiles is complex data, and has two pieces of information of phase distribution and intensity distribution. Assuming that the excitation profile at the time of positive polarity is Pre_positive( ) and the excitation profile at the time of negative polarity is Pre_negative( ), the intensity distribution at the time of positive polarity Amp_positive(x) and the intensity distribution at the time of negative polarity Amp_negative( ) are obtained by Expressions (10) and Expression (11), respectively.

[Expression 10]

$$\text{Amp\_positive}(x) = \sqrt{P\text{Re\_positive}(real, x)^2 + P\text{Re\_positive}(imgn, x)^2} \quad (10)$$

[Expression 11]

$$\text{Amp\_negative}(x) = \sqrt{P\text{Re\_negative}(real, x)^2 + P\text{Re\_negative}(imgn, x)^2} \quad (11)$$

Here, x is a discrete point number indicating the position in a slice direction, real is a symbol indicating a real part, and imgn is a symbol indicating an imaginary part.

Figure 15:
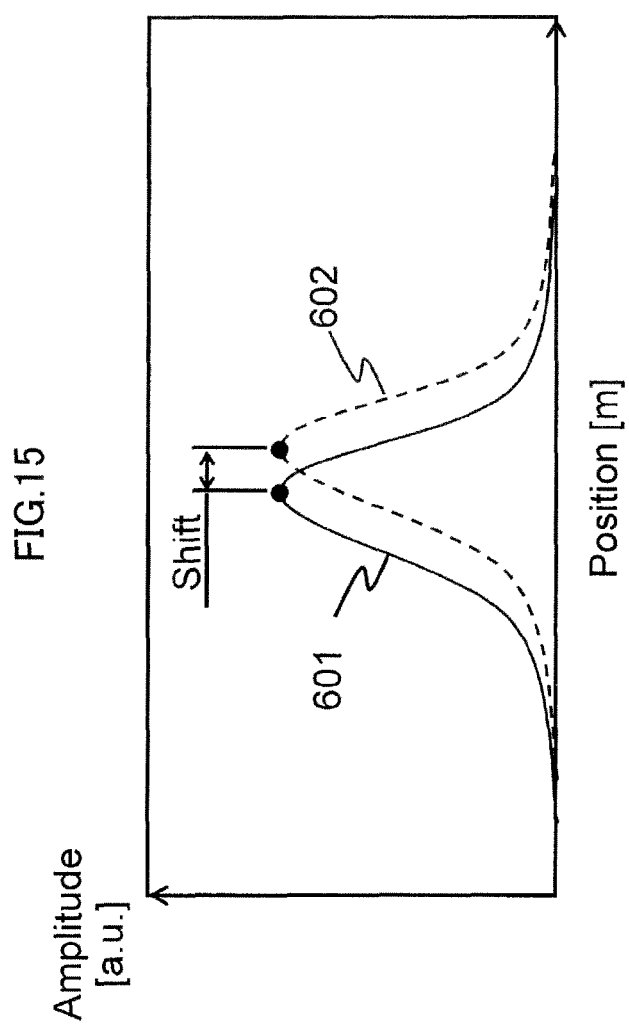
FIG. 15 is an explanatory view for explaining a method of calculating the shift amount of the excitation position of the second embodiment.

The shift amount calculation section 717 calculates a position shift Shift between the maximum value of the intensity distribution of an excitation profile 601 at the time of positive polarity and the maximum value of the intensity distribution of an excitation profile 602 at the time of negative polarity, which is shown in a conceptual diagram of FIG. 15, as the shift amount Shift of the excitation position. That is, the shift amount Shift of the excitation position is calculated, for example, according to Expressions (12) to (14) using the intensity distribution Amp_positive(x) and Amp_negative(x)

[Expression 12]

$$\text{Shift} = \frac{MaxPositionPositive - MaxPositionNegative}{2} \quad (12)$$

[Expression 13]

$$MaxPositionPositive = \quad (13)$$
$$\{x \mid \text{Amp\_positive}(x) = \text{Max}(\text{Amp\_positive}(x))\}$$

[Expression 14]

$$MaxPositionNegative = \quad (14)$$
$$\{x \mid \text{Amp\_negative}(x) = \text{Max}(\text{Amp\_positive}(x))\}$$

Here, x indicates a discrete point number in a slice direction, Max( ) indicates a function to return the maximum value in the designated data column, MaxPositionPositive indicates a position of the maximum value of the excitation profile of the positive polarity, and MaxPositionNegative indicates a position of the maximum value of the excitation profile of the negative polarity.

The first-order phase difference calculation section 716 calculates a coefficient of the first-order term of the difference between the phase of the positive polarity data and the phase of the negative polarity data as a first-order phase difference using the excitation profiles Pre_positive( ) and Pre_negative( ).

Specifically, a phase difference Phase_complex(x) between the positive polarity data and the negative polarity data is first calculated according to the following Expression (15). In addition, the phase difference Phase_complex (x) is complex data.

[Expression 15]

$$\text{Phase\_complex}(x) = \text{Pre\_positive}(x) \times \text{Conjugate}[\text{Pre\_negative}(x + \text{shift})] \quad (15)$$

Here, Conjugate[ ] is a function indicating complex conjugate processing, and Shift is an excitation position shift amount between the positive polarity data and the negative polarity data calculated by Expression (12).

A phase value Phase_scalar(x) is calculated from the calculated Phase_complex(x) according to the following Expression (16). The phase value Phase_scalar(x) that is calculated is scalar data.

[Expression 16]

$$\text{Phase\_scalar}(x) = \text{Phase\_scalar}(x - 1) + \quad (16)$$
$$\text{Phase}[\text{Phase\_complex}(x) + \text{Conjugate}[\text{Phase\_complex}(x + 1)]]$$

Here, Phase[ ] is a function to return the phase value of complex data. The reason why the phase value is not calculated directly from Phase_complex(x) is to prevent phase aliasing.

A calculated phase value Phase_scalar(x) 611 changes as shown in FIG. 16(*a*). That is, the phase is changed by 360

[deg] with the center (almost matching the position of the maximum value of the intensity distribution) 620 of the excitation range as a boundary. This is because the positive polarity data and the negative polarity data have a change of 180 [deg] in opposite phases as shown in FIG. 4 and the phase difference between the positive polarity data and the negative polarity data occurs. The first-order phase difference is the inclination of the calculated phase value Phase_scalar(x) 611. In order to calculate the first-order phase difference (inclination), it is necessary to exclude phase changes with the center 620 of the excitation range as a boundary and perform phase unwrap processing.

Therefore, a phase value after phase unwrap processing Phase_unwraped(x) is first calculated for the phase value Phase_scalar(x) except for data of a section 621 (for example, a range of the excitation slice thickness), in which a phase change occurs with the center of the excitation range as a boundary, by the following Expressions (17) and (18).

[Expression 17]

$$\text{Phase\_unwraped}(x) = \begin{cases} \text{Phase\_scalar}(x) + 360 & \text{if(Difference} < -360) \\ \text{Phase\_scalar}(x) - 360 & \text{if(Difference} > +360) \\ \text{Phase\_scalar}(x) & \text{if}(-360 < \text{Difference} < 360) \end{cases} \quad (17)$$

[Expression 18]

$$\text{Difference} = \text{Phase\_scalar}(x) - \text{Phase\_scalar}(\text{PreviousPoint}) \quad (18)$$

Here, x indicates a section other than the section 621 where a phase change occurs, and PreviousPoint indicates a last x position.

By the phase unwrap processing, a phase distribution 612 shown in FIG. 16(b) is eventually obtained.

The first-order phase difference calculation section 716 determines an approximate first-order straight line using the least square method for the phase distribution, and calculates the inclination as a first-order phase difference FirstOrderPhase. Specifically, the first-order phase difference FirstOrderPhase is calculated according to the following Expression (19).

[Expression 19]

$$FirstOrderPhase = \frac{\sum \text{Phase\_unwraped}(x) \cdot \sum x^2 - (x \cdot \text{Phase\_unwraped}(x)) \cdot \sum x}{N \sum x^2 - (\sum x)^2} \quad (19)$$

Here, N indicates the number of data points used in fitting processing. In addition, fitting based on the least square method is performed except for the section 621 where a phase change occurs.

Similar to the first embodiment, the refocusing pulse application amount calculation section 712 of the present embodiment calculates the application amount of the refocusing pulse of each of the slice gradient magnetic fields 211 and 212 as a correction value. However, although the refocusing pulse application amount is calculated by calculating the surplus application amount from the slice gradient magnetic field waveform in the first embodiment, the refocusing pulse application amount is calculated using the first-order phase difference FirstOrderPhase in the present embodiment.

The refocusing pulses 251 and 252 are pulses having opposite polarities. Here, it is assumed that both refocusing pulses 251 and 252 have the same area. When the refocusing areas of the slice gradient magnetic fields 211 and 212 are changed by the refocusing pulses 251 and 252, the inclination of the first-order phase difference of the excitation profile is changed. Using this, the refocusing area, that is, the application amount of each of the refocusing pulses 251 and 252 is calculated so as to produce the inclination of the phase to cancel out the calculated first-order phase difference FirstOrderPhase.

Specifically, the application amounts (areas) Adjust_Area_251 and Adjust_Area_252 [s·T/m] of the refocusing pulses 251 and 252 are calculated according to the following Expressions (20) and (21), respectively.

[Expression 20]

$$\text{Adjust\_Area\_251} = FirstOrderPhase \cdot \frac{1}{2\pi} \cdot \text{Duration} \cdot GcAmp \times \frac{1}{2} \quad (20)$$

[Expression 21]

$$\text{Adjust\_Area\_252} = -FirstOrderPhase \cdot \frac{1}{2\pi} \cdot \text{Duration} \cdot GcAmp \times \frac{1}{2} \quad (21)$$

Here, FirstOrderPhase is a first-order phase difference [deg] calculated by Expression (19), Duration is the sampling time [s] of the echo signals 541 and 542 obtained by the excitation profile measurement sequence 500 shown in FIG. 14, and GcAmp is the strength [T/m] of the readout encoding gradient magnetic fields 531 and 532.

Similar to the first embodiment, the irradiation frequency calculation section 713 of the present embodiment calculates the irradiation frequencies of the half RF pulses 201 and 202 as correction values. In the first embodiment, a position shift of each slice selection excitation position is determined from the slice gradient magnetic field strength and the irradiation frequency is calculated so as to eliminate the position shift. In the present embodiment, however, a position shift is determined from the calculated excitation position shift amount Shift to calculate the irradiation frequency.

As the irradiation frequency, a Larmor frequency of the designated slice position is usually set. However, when the excitation position is shifted between the positive polarity data and the negative polarity data, it is necessary to match the excitation position of the positive polarity data and the excitation position of the negative polarity data to each other by changing the irradiation frequencies of the half RF pulses 201 and 202 by the shift amount. The irradiation frequency calculation section 713 of the present embodiment calculates irradiation frequencies to match these excitation positions.

The irradiation frequency is calculated for each of the half RF pulse 201, which is applied together with the positive polarity slice gradient magnetic field 211, and the half RE pulse 202, which is applied together with the negative polarity slice gradient magnetic field 212. This calculation is performed according to the following Expressions (22) and (23).

[Expression 22]

$$\text{Frequency\_Positive} = \gamma \cdot Gs \cdot \left(\text{Offcenter} + \frac{\text{Shift}}{2}\right) + \gamma \cdot GcBase \quad (22)$$

[Expression 23]

$$\text{Frequency\_Negative} = \gamma \cdot Gs \cdot \left(\text{Offcenter} - \frac{\text{Shift}}{2}\right) + \gamma \cdot GcBase \quad (23)$$

Here, Frequency_Positive is an irradiation frequency [Hz] of the half RF pulse when the slice gradient magnetic field has a positive polarity, Frequency_Nagative is an irradiation frequency [Hz] of the half RF pulse when the slice gradient magnetic field has a negative polarity, γ is a gyromagnetic ratio [Hz/T], Gs is a slice gradient magnetic field strength [T/m], Offcenter is a distance [m] from the magnetic field center to the designated slice position, Shift is an excitation position shift amount between the positive polarity data and the negative polarity data calculated by the above Expression (12), and GcBase is a static magnetic field strength [T].

The zero-order phase difference calculation section 714 of the present embodiment calculates a zero-order phase difference between the positive polarity data and the negative polarity data as a correction value. Although the zero-order phase difference is calculated from the slice gradient magnetic field waveform in the first embodiment, the zero-order phase difference is calculated by the following Expression (24) using the phase value after phase unwrap processing Phase_unwraped(x) obtained from the excitation profile at the time of positive polarity and the excitation profile at the time of negative polarity in the present embodiment.

[Expression 24]

$$ZerothOrderPhase = 180 - \frac{N\sum(x \cdot \text{Phase\_unwraped}(x)) - \sum x \cdot \sum \text{Phase\_unwraped}(x)}{N\sum x^2 - (\sum x)^2} \quad (24)$$

Here, x is when a section 1501 where a phase change occurs is excluded.

The value calculated from Expression (24) is a value obtained by subtracting a phase difference except for the inclination of the first-order phase from the phase difference between the positive polarity data and the negative polarity data from 180 [deg]. When the phase difference between the positive polarity data and the negative polarity data is 180 [deg], side lobe signals thereof are canceled out. Therefore, a difference of the phase difference between the positive polarity data and the negative polarity data from 180 [deg] is calculated as the zero-order phase difference.

The flow of the above pre-processing by each section of the pre-processing unit 710 of the present embodiment will be described with reference to FIG. 17. Here, the total number of slices is set to N. Also in the present embodiment, the pre-processing unit 710 performs pre-processing for calculating a correction value for each slice. Here, a case where the measurement of the excitation profile is performed for all slices and then the correction value is calculated for each slice will be described as an example.

The excitation profile measurement section 715 acquires the excitation profile Pre_positive( ) when the slice gradient magnetic field has a positive polarity and the excitation profile Pre_negative( ) when the slice gradient magnetic field has a negative polarity by executing the excitation profile measurement sequence 500 using the imaging parameter at the time of main measurement for each slice (steps S2101 to S2104).

Then, the pre-processing unit 710 repeats the process of steps S2106 to S2110 by the iterative process (steps S2105 and S2211). The number of repetitions is assumed to be the number of slices (here, N) designated as the imaging conditions of the main measurement. Here, the number of slices to be processed during the repetitive processing is expressed as i.

First, the shift amount calculation section 717 calculates the shift amount Shift of the excitation position at the i-th slice position from both the excitation profiles at the i-th slice position using the above Expressions (12) to (14) (step S2106). Then, the first-order phase difference calculation section calculates the first-order phase difference FirstOrderPhase at the i-th slice position from both the excitation profiles at the i-th slice position using the above Expressions (15) to (19) (step S2107).

Then, the refocusing pulse application amount calculation section 712 calculates the application amounts of the refocusing pulses 251 and 252 with respect to each slice gradient magnetic field at the i-th slice position according to the above Expressions (20) and (21) using the first-order phase difference FirstOrderPhase at the i-th slice position, respectively (step S2108).

Then, the irradiation frequency calculation section 713 calculates the irradiation frequencies of the half RF pulses 201 and 202 at the i-th slice position according to the above Expressions (22) and (23) using the calculated shift amount Shift (step S2109).

Then, the zero-order phase determination section calculates a zero-order phase difference between the positive polarity data and the negative polarity data at the i-th slice position according to the above Expression (24) using the first-order phase difference FirstOrderPhase at the i-th slice position (step S2110).

The pre-processing unit 710 of the present embodiment performs pre-processing as described above, thereby calculating the correction values of the irradiation frequencies of the half RF pulses 201 and 202, the correction values of the application amounts of the refocusing pulses 251 and 252, and the correction value of the zero-order phase difference.

In addition, in the pre-processing described above, any of the irradiation frequency, the refocusing pulse application amount, and the zero-order phase difference may be calculated first.

In addition, since the main measurement processing of the present embodiment is the same as that in the first embodiment, explanation thereof will not be given herein.

Here, FIGS. 18(a) to 18(g) show the intensity distribution of the excitation profile obtained by the excitation profile measurement sequence 500.

Figure 18:
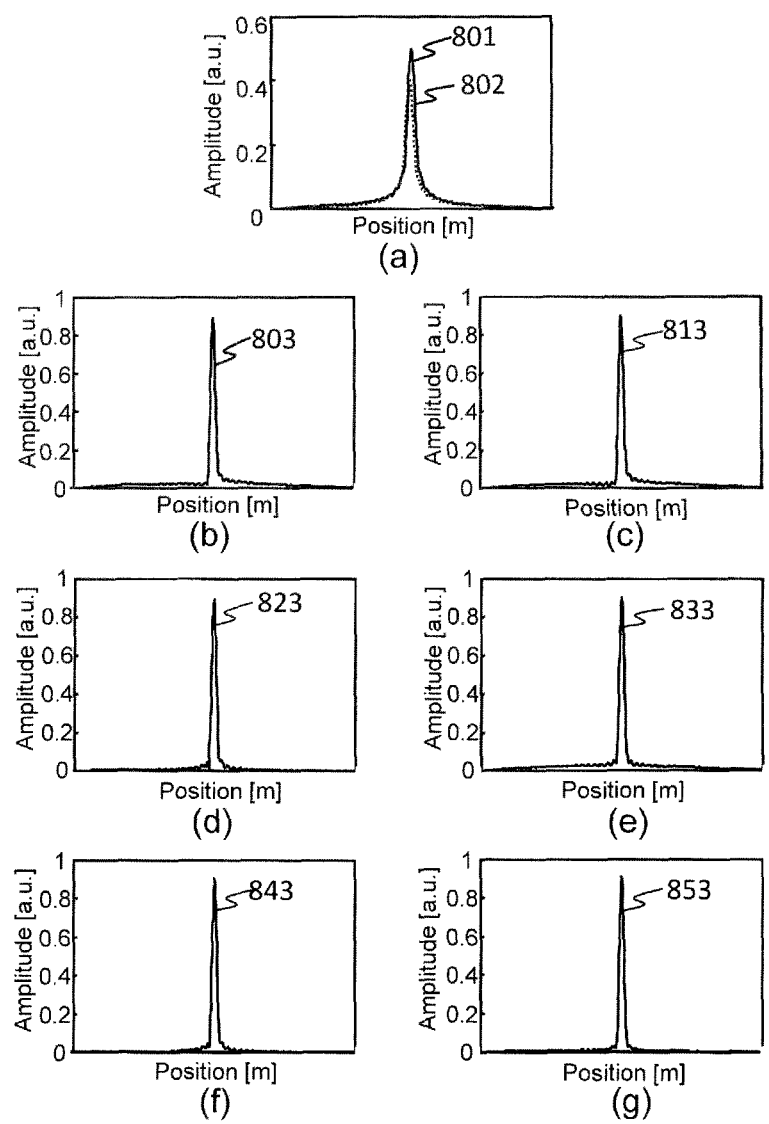
FIGS. 18($a$) to 18($g$) are explanatory views for explaining the improvement effect of the excitation profile when a correction value is used in the second embodiment.

FIG. 18(a) is intensity distributions 801 and 802 of the excitation profiles of positive polarity data and negative polarity data that are obtained by executing the excitation profile measurement sequence 500 using the irradiation frequency and the refocusing pulse application amount set by the imaging parameter. FIG. 18(b) is an intensity distribution 803 of the excitation profile of polarity-added data obtained by adding positive polarity data and negative polarity data that are obtained by executing the excitation profile measurement sequence 500 using the irradiation frequency and the refocusing pulse application amount set by the imaging parameter.

FIG. 18(c) is an intensity distribution 813 of the excitation profile of polarity-added data obtained by changing the irradiation frequency to the correction value and executing the excitation profile measurement sequence 500. FIG. 18(d) is an intensity distribution 823 of the excitation profile of polarity-added data obtained by changing the refocusing pulse application amount to the correction value and executing the excitation profile measurement sequence 500. FIG. 18(e) is an intensity distribution 833 of the excitation profile of polarity-added data obtained by correcting positive polarity data and negative polarity data, which are obtained by executing the excitation profile measurement sequence 500 using the irradiation frequency and the refocusing pulse application amount set by the imaging parameter, using the zero-order phase difference and then adding the corrected positive and negative polarity data. FIG. 18(f) is an intensity distribution 843 of the excitation profile of polarity-added data obtained by changing the irradiation frequency and the refocusing pulse application amount to the correction values and executing the excitation profile measurement sequence 500. FIG. 18(g) is an intensity distribution 853 of the excitation profile of polarity-added data obtained by correcting positive polarity data and negative polarity data, which are obtained by changing the irradiation frequency and the refocusing pulse application amount to the correction values and executing the excitation profile measurement sequence 500, using the zero-order phase difference and adding the corrected positive and negative polarity data.

As can be seen from these diagrams, since a steep excitation profile is obtained by adjusting the excitation position shift amount (irradiation frequency), the first-order phase difference (refocusing pulse application amount), and the zero-order phase difference, mixing of signals from positions other than the designated slice position can be suppressed. In particular, it can be seen that the adjustment of the first-order phase difference (adjustment of the refocusing pulse application amount) is effective.

Although the excitation profiles measured in the pre-processing are shown in FIGS. 18(a) to 18(e) for the sake of explanation, the same can be said for the main measurement. FIGS. 19(a) and 19(b) show images obtained by reconstructing the data acquired by main measurement processing. An object to be imaged is a conical nickel chloride aqueous solution phantom, and the imaging cross-section is set so that the diameter of the circle is changed in a slice direction.

An image 861 shown in FIG. 19(a) is a resulting image when main measurement has been performed without using three correction values (irradiation frequency, refocusing pulse application amount, and zero-order phase difference) obtained by pre-processing, and an image 862 is a resulting image obtained by reflecting each correction value determined by the above-described method. In addition, a profile 871 shown in FIG. 19(c) is a profile of the position shown by the dotted line on the image 861, and a profile 872 shown in FIG. 19(d) is a profile of the position shown by the dotted line on the image 862.

In the image 861, mixing of signals from positions other than the designation slice position is observed as shown by the arrow. However, it can be seen that the signals can be reduced in the image 862. This can be similarly seen from the shapes of the profiles 871 and 872 of the respective images.

In addition, although the example where the shift amount from the position of the maximum value of the intensity distribution is calculated is shown as the calculation of the shift amount Shift (Expression (12)) by the irradiation frequency calculation section 713 in the present embodiment, the present invention is not limited thereto. As other examples, a value that maximizes a cross-correlation value between the intensity distributions Amp_positive(x) and Amp_negative(x) may be calculated as the shift amount Shift. In addition, the shift amount Shift may be calculated from the inclination of the phase difference on space after a Fourier transform of the intensity distributions Amp_positive(x) and Amp_negative(x).

In addition, also in the present embodiment, in the case of an MRI apparatus in which an excitation position shift is difficult to occur, it is not necessary to perform shift amount calculation and irradiation frequency calculation. In this case, therefore, the shift amount calculation section 717 and the irradiation frequency calculation section 713 may not be provided. In addition, in this case, the value of the variable Shift in Expression (15) to calculate the phase difference Phase_complex(x) is assumed to be 0 In addition, it is assumed that the irradiation frequency used in the main measurement is designated by the imaging parameter.

In addition, also in the present embodiment, when it is known that the zero-order phase difference does not significantly affect the image quality, it is not necessary to perform addition processing in consideration of the zero-order phase difference. In this case, the zero-order phase difference calculation section 714 may not be provided. When addition processing is not performed, 0 [deg] may be set as a phase difference.

As described above, according to the present embodiment, there is provided a magnetic resonance imaging apparatus including: a static magnetic field generation system 120; a measurement system including a gradient magnetic field generation system 130, a high frequency magnetic field generation system 150, and a high frequency magnetic field detection system 160; and an arithmetic system 170 that controls an operation of the measurement system according to a pulse sequence to measure a nuclear magnetic resonance signal and performs calculation using data obtained from the nuclear magnetic resonance signal. The pulse sequence is an ultra-short echo time sequence to obtain each echo signal by performing two slice selection excitations by inverting a polarity of a slice gradient magnetic field, which is applied together with a half RF pulse, between a positive polarity and a negative polarity. The arithmetic system 170 includes a pre-processing unit 710 that calculates a correction value used in the measurement and the calculation and a main measurement unit 720 that sets the correction value calculated by the pre-processing unit 710 in the pulse sequence and performs main measurement by controlling the measurement system according to the pulse sequence after the setting so that an image is reconstructed. The pre-processing unit 710 includes a refocusing pulse application amount calculation section 712 that calculates an application amount of a refocusing pulse of each slice gradient magnetic field as the correction value. The main measurement unit 720 includes an image reconstruction section 721 that adds positive polarity data, which is an echo signal obtained when the slice gradient magnetic field having a positive polarity is applied, and negative polarity data, which is an echo signal obtained when the slice gradient magnetic field having a negative polarity is applied, in the main measurement and reconstructs an image using polarity-added data after the addition. The refocusing pulse application amount calculation section 712 calculates the application amount of each refocusing pulse so as to reduce a side lobe signal of an excitation profile after adding the positive polarity data and the negative polarity data.

In addition, the pre-processing unit further includes an excitation profile measurement section 715 that measures excitation profiles of the positive polarity data and the negative polarity data and a first-order phase difference calculation section 716 that calculates a coefficient of a first-order term of the phase difference as a first-order phase difference using the excitation profiles. The refocusing pulse application amount calculation section 712 determines each refocusing pulse application amount using the first-order phase difference.

In general, when the excitation profiles of the positive polarity data and the negative polarity data do not have phase distributions that are 180 [deg] inverted with respect to each other in their side lobe portions, side lobe of the excitation profile remains. In the present embodiment, however, the phase difference between the positive polarity data and the negative polarity data is calculated, and the first-order phase difference is corrected by adjusting the refocusing pulse application amount of the slice gradient magnetic field pulse.

Accordingly, since the side lobe signal of the excitation profile can be effectively suppressed, the excitation profile of polarity-added data can be made as a good excitation profile that is steep and has a small amount of side lobe. As a result, it is possible to prevent the mixing of signals from positions other than the designated slice position in a reconstructed image. Therefore, it is possible to obtain a high-quality reconstructed image in which artifacts are suppressed.

In addition, the pre-processing unit 710 may further include an irradiation frequency calculation section 713 that calculates each irradiation frequency of the half RF pulse as the correction value and a shift amount calculation section 717 that calculates an excitation position shift amount between the excitation profiles. In this case, the irradiation frequency calculation section 713 calculates each irradiation frequency so as to eliminate a position shift between the two slice selection excitation positions, and the position shift is calculated using the shift amount.

In general, when a position shift occurs between the intensity distributions of positive polarity data and negative polarity data, the width of the main lobe of the excitation profile is increased and a side lobe signal remains. In the present embodiment, however, by measurement of the excitation profile in pre-processing, the excitation position shift amount between the positive polarity data and the negative polarity data is calculated, the irradiation frequencies of the half RF pulses 201 and 202 are adjusted, and an excitation position shift is corrected.

In addition, the pre-processing unit 710 may further include a zero-order phase difference calculation section 714 that calculates a zero-order phase difference, which is a zero-order term of a phase difference between the positive polarity data and the negative polarity data, as the correction value. In this case, the zero-order phase difference calculation section 714 calculates the zero-order phase difference using each excitation profile. In addition, the image reconstruction section 721 corrects a phase difference between the positive polarity data and the negative polarity data using the zero-order phase difference before the addition.

Thus, in the present embodiment, the zero-order phase difference is corrected by performing phase addition at the time of addition processing after acquiring the main measurement data.

According to the present embodiment, a steep excitation profile was obtained by each of these processes. As a result, a reconstructed image in which artifacts are suppressed is obtained with signals from positions other than the designated slice position not being mixed into the reconstructed image.

In addition, also in the present embodiment, the pre-processing may be performed immediately before the main measurement, or may be performed at the time of installation work of the apparatus. When the pre-processing is performed at the time of installation work of the apparatus, the pre-processing is performed under the conditions of the combination of all slice positions and slice thicknesses designated in the main measurement processing. Alternatively, it is also possible to perform the pre-processing under only the representative conditions. In any case, the obtained excitation position shift amount and first-order phase difference or the obtained refocusing pulse application amount, irradiation frequency, and zero-order phase difference are stored in the storage device 172 or the like so as to match the calculation conditions.

In addition, in the embodiment described above, the pre-processing is divided into two processes of excitation profile measurement processing and correction value calculation processing using the measured excitation profile, and each process is repeated by the number of slices. This is because measurement of the excitation profile under the same measurement conditions as in the main measurement is taken into consideration. That is, when the excitation of a plurality of slices is performed within the repetition time (TR) using a multi-slice method or the like, time to calculate a correction value may not be obtained. Thus, it is possible to obtain a correction value with higher accuracy by performing a slice excitation under the same conditions as in the main measurement processing.

However, when the calculation time of each correction value in steps S2106 to S2110 can be secured after the excitation of each slice and the measurement of the excitation profile, it is not necessary to divide the repetitive processing into two processes. The measurement of the excitation profile and the calculation of the correction value may be performed as a series of processing for each slice.

Third Embodiment

Next, a third embodiment to which the present invention is applied will be described. The present embodiment is characterized in that the optimal zero-order and first-order phase differences are searched for and calculated on the basis of the signal amount of side lobe of the excitation profile.

The MRI apparatus 100 of the present embodiment has basically the same configuration as in the first embodiment. However, since a method of calculating the zero-order phase difference and the first-order phase difference is different, the configurations of the pre-processing unit 710 of the arithmetic system 170 is different.

Figure 20:
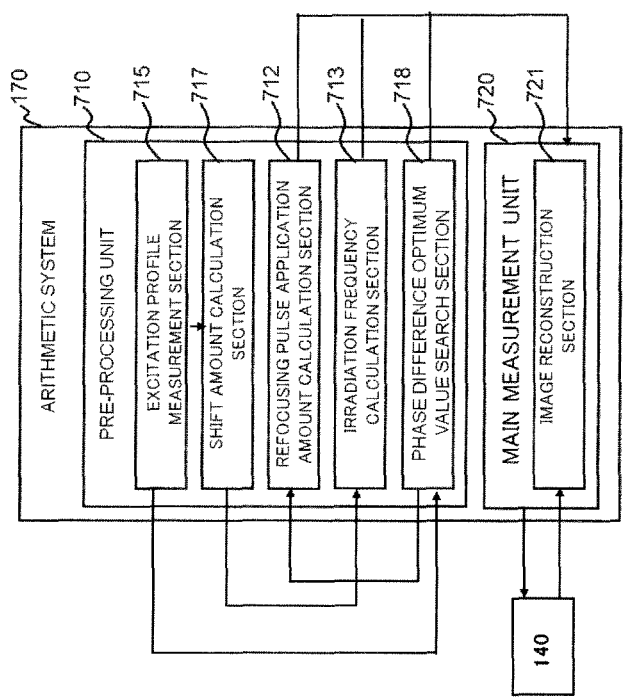
FIG. 20 is a functional block diagram of an arithmetic system of a third embodiment.

As shown in FIG. 20, the pre-processing unit 710 of the present embodiment includes an excitation profile measurement section 715, a shift amount calculation section 717, a refocusing pulse application amount calculation section 712, an irradiation frequency calculation section 713, and a phase difference optimum value search section 718. In addition, similar to the second embodiment, the arithmetic system 170 includes the pre-processing unit 710 and the main measurement unit 720, and the main measurement unit 720 includes the image reconstruction section 721.

In addition, each processing of the excitation profile measurement section 715, the shift amount calculation section 717, and the irradiation frequency calculation section 713 of the present embodiment is the same as that in the second embodiment. In addition, irradiation frequency calculation based on the flow of pre-processing of the pre-processing unit 710 of the present embodiment is basically the same as that in the second embodiment. That is, as shown in FIG. 17, the irradiation frequency is calculated by measuring the excitation profile for each slice position and calculating the shift amount of the excitation position using the measured excitation profile.

The phase difference optimum value search section 718 of the present embodiment searches for a value (optimal value) that minimizes an evaluation value by changing the zero-order phase difference and the first-order phase difference from the initial values set in advance according to the rule set in advance. In addition, the obtained optimal values are set as the zero-order phase difference and the first-order phase difference. In this case, the signal amount of side lobe obtained from each excitation profile is used as the evaluation value.

In addition, the refocusing pulse application amount calculation section 712 of the present embodiment calculates the application amount of the refocusing pulse using the first-order phase difference, which is obtained as the optimal value by the phase difference optimum value search section 71B, in the same procedure as in the second embodiment described above. In addition, the image reconstruction section 721 corrects the polarity-added data using the zero-order phase difference obtained as the optimal value by the phase difference optimum value search section 718.

Figure 17:
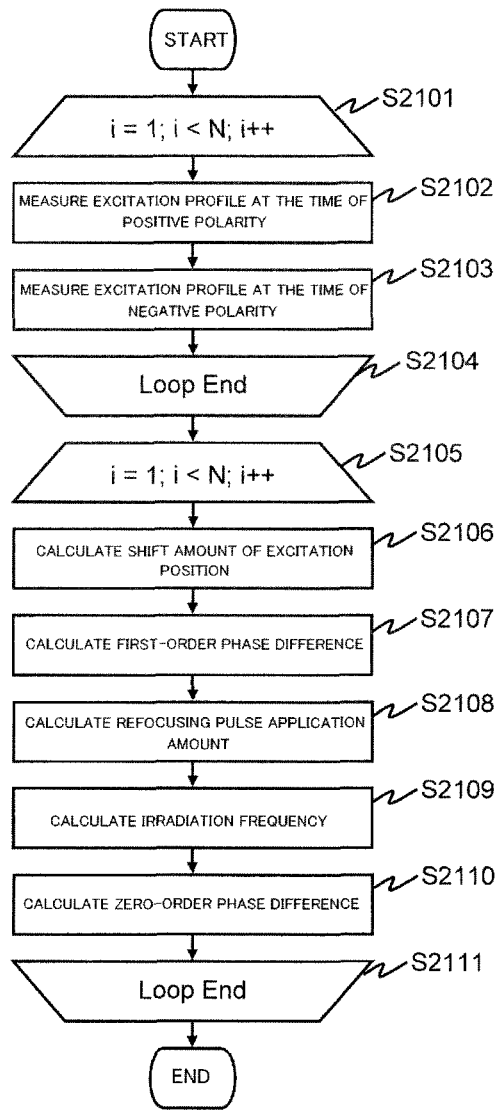
FIG. 17 is a flow chart of pre-processing of the second embodiment.

The flow of the pre-processing of the pre-processing unit 710 of the present embodiment is basically the same as the flow of the pre-processing of the second embodiment shown in FIG. 17. However, processing for searching for the optimal values of the zero-order phase difference and the first-order phase difference by the phase difference optimum value search section 71B is performed instead of the first-order phase difference calculation processing of the first-order phase difference calculation section 716 in step S2107, and the zero-order phase difference and the first-order phase difference are calculated herein. Therefore, in the present embodiment, zero-order phase difference calculation processing in step S2110 is not performed. In addition, main measurement processing of the present embodiment is the same as that in the first embodiment.

Figure 21:
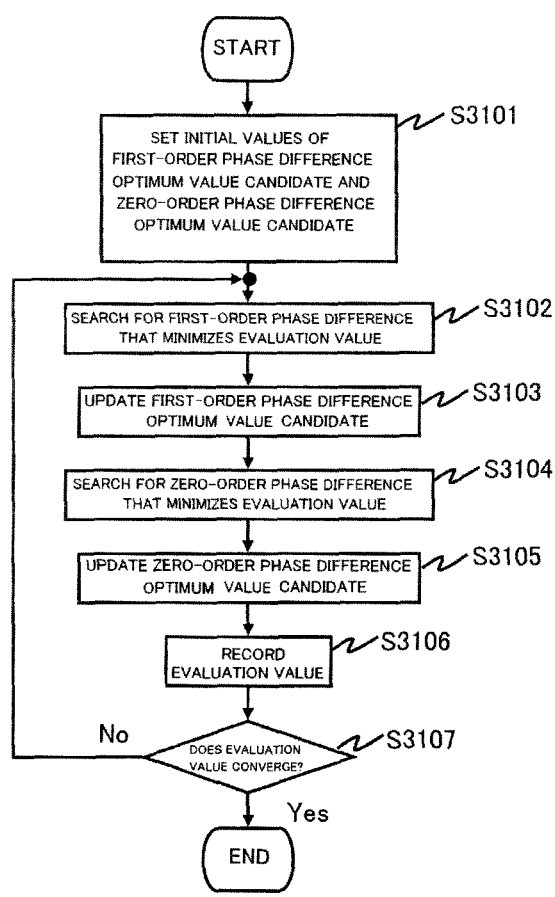
FIG. 21 is a flow chart of zero-order phase difference calculation processing and first-order phase difference calculation processing of the pre-processing in the third embodiment.

Hereinafter, the flow of the process of searching for the optimal values of the zero-order phase difference and the first-order phase difference by the phase difference optimum value search section 718 of the present embodiment will be described with reference to the flowchart of FIG. 21.

First, the phase difference optimum value search section 718 sets the initial values of the zero-order phase difference and the first-order phase difference, which are set in advance, as a zero-order phase difference optimum value candidate and a first-order phase difference optimum value candidate (step S3101). Here, for example, 0 [deg] is set as the initial value. In addition, when a value close to the optimal value is known in advance from the characteristic of the device, it is possible to set the value.

Then, the phase difference optimum value search section 718 searches for a first-order phase difference that minimizes the signal amount of side lobe (step S3102), and updates the optimal value candidate of the first-order phase difference (step S3103).

The signal amount of side lobe (hereinafter, referred to as a side lobe amount) SideLobeValue is defined by the following Expressions (25), for example.

[Expression 25]

$$\text{SideLobeValue} = \Sigma\{\text{Amp\_composed}(x) | x \notin \text{MainLobeRange}\} \quad (25)$$

Here, Amp_composed( ) is data obtained by adding the excitation profile at the time of positive polarity Pre_positive( ) and the excitation profile at the time of negative polarity Pre_negative( ) which are obtained by pre-processing, in a state where the zero-order phase difference and the first-order phase difference at this time are set, and is obtained by the following Expressions (26) to (30). In addition, Pre_negative( ) in the following expressions is treated as a shift by the shift amount calculated by the shift amount calculation section 717.

[Expression 26]

$$\text{Amp\_composed}(x) = \sqrt{\begin{aligned}&(P\text{Re\_positive}'(\text{real}, x) + P\text{Re\_negative}'(\text{real}, x))^2 + \\ &(P\text{Re\_positive}'(\text{imgn}, x) + P\text{Re\_negative}'(\text{imgn}, x))^2\end{aligned}} \quad (26)$$

[Expression 27]

$$P\text{Re\_positive}'(\text{real}, x) = \\ P\text{Re\_positive}(\text{real}, x) \cdot \cos(\text{ZerothOrderPhase} + \\ \text{FirstOrderPhase} \times x) + P\text{Re\_positive}(\text{imgn}, x) \cdot \\ \sin(\text{ZerothOrderPhase} + \text{FirstOrderPhase} \times x) \quad (27)$$

[Expression 28]

$$P\text{Re\_positive}'(\text{imgn}, x) = \\ P\text{Re\_positive}(\text{imgn}, x) \cdot \cos(\text{ZerothOrderPhase} + \\ \text{FirstOrderPhase} \times x) - P\text{Re\_positive}(\text{real}, x) \cdot \\ \sin(\text{ZerothOrderPhase} + \text{FirstOrderPhase} \times x) \quad (28)$$

[Expression 29]

$$P\text{Re\_negative}'(\text{real}, x) = \\ P\text{Re\_negative}(\text{real}, x) \cdot \cos(\text{ZerothOrderPhase} + \\ \text{FirstOrderPhase} \times x) + P\text{Re\_negative}(\text{imgn}, x) \cdot \\ \sin(\text{ZerothOrderPhase} + \text{FirstOrderPhase} \times x) \quad (29)$$

[Expression 30]

$$P\text{Re\_negative}'(\text{imgn}, x) = \\ P\text{Re\_negative}(\text{imgn}, x) \cdot \cos(\text{ZerothOrderPhase} + \\ \text{FirstOrderPhase} \times x) - P\text{Re\_negative}(\text{real}, x) \cdot \\ \sin(\text{ZerothOrderPhase} + \text{FirstOrderPhase} \times x) \quad (30)$$

Here, x is a discrete point number indicating the position in a slice direction, real is a symbol indicating a real part, imgn is a symbol indicating an imaginary part, ZerothOrderPhase is a zero-order phase difference, and FirstOrderPhase is a first-order phase difference.

In addition, MainLobeRange in Expression (25) is a range of main lobe, and is defined by the following Expression (31), for example.

[Expression 31]

$$\text{Offcenter} - \text{Thickness} < \text{MainLobeRange} < \text{Offcenter} + \text{Thickness} \quad (31)$$

Offcenter is a distance [m] from the magnetic field center to the designated slice position, and Thickness is a designated slice thickness [m].

In the search for the first-order phase difference that minimizes the side lobe amount of Expression (25), the side lobe amount is calculated while changing the first-order phase difference in units of 0.1 [deg] in a sufficiently wide range, for example, in a range of −3600 [deg] to 3600 [deg], and the first-order phase difference that minimizes the side lobe amount is set as an optimal value candidate of the first-order phase difference.

After setting the first-order phase difference as an optimal value candidate as FirstOrderPhase, the phase difference optimum value search section 718 searches for a zero-order phase difference that minimizes the side lobe amount (step S3104), and updates the optimal value candidate of the zero-order phase difference (step S3105). The search method is the same as the search for the first-order phase difference. However, since this is for the zero-order phase, the search range is set to −180 [deg] to 180 [deg]. The side lobe amount is calculated while changing this range in units of 0.1 [deg], and the zero-order phase difference that minimizes the side lobe amount is set as an optimal value candidate.

The phase difference optimum value search section 718 stores the side lobe amount, which is the calculated evaluation value, so as to match the number of times of calculation of the zero-order phase difference (step S3106).

Then, the phase difference optimum value search section 718 determines whether or not the change in the side lobe amount, which is the evaluation value, converges (step S3107). The convergence of the change in the side lobe amount is defined by the following Expression (32), for example.

[Expression 32]

$$0.1 > \left(1 - \frac{SideLobeValue(n)}{SideLobeValue(n-1)}\right) \times 100 \quad (32)$$

Here, SideLobeValue(n) indicates a side lobe amount recorded at the n-th time.

Expression (32) shows the convergence conditions when the change in the side lobe amount is less than 0.1 [%] while repeating the process of searching for the zero-order phase difference and the first-order phase difference. In addition, in step S3107, the phase difference optimum value search section 718 needs to repeat the process at least twice for comparison with the side lobe amount recorded on the last search.

The phase difference optimum value search section 718 ends the optimal value search process when the Expression (32) is satisfied. In addition, optimal value candidates of the zero-order phase difference and the first-order phase difference at that time are set as a zero-order phase difference and a first-order phase difference.

As described above, according to the present embodiment, there is provided a magnetic resonance imaging apparatus including: a static magnetic field generation system 120; a measurement system including a gradient magnetic field generation system 130, a high frequency magnetic field generation system 150, and a high frequency magnetic field detection system 160; and an arithmetic system 170 that controls an operation of the measurement system according to a pulse sequence to measure a nuclear magnetic resonance signal and performs calculation using data obtained from the nuclear magnetic resonance signal. The pulse sequence is an ultra-short echo time sequence to obtain each echo signal by performing two slice selection excitations by inverting a polarity of a slice gradient magnetic field, which is applied together with a half RF pulse, between a positive polarity and a negative polarity. The arithmetic system 170 includes a pre-processing unit 710 that calculates a correction value used in the measurement and the calculation and a main measurement unit 720 that sets the correction value calculated by the pre-processing unit 710 in the pulse sequence and performs main measurement by controlling the measurement system according to the pulse sequence after the setting so that an image is reconstructed. The pre-processing unit 710 includes a refocusing pulse application amount calculation section 712 that calculates an application amount of a refocusing pulse of each slice gradient magnetic field as the correction value. The main measurement unit 720 includes an image reconstruction section 721 that adds positive polarity data, which is an echo signal obtained when the slice gradient magnetic field having a positive polarity is applied, and negative polarity data, which is an echo signal obtained when the slice gradient magnetic field having a negative polarity is applied, in the main measurement and reconstructs an image using polarity-added data after the addition. The refocusing pulse application amount calculation section 712 calculates the application amount of each refocusing pulse so as to reduce a side lobe signal of an excitation profile after adding the positive polarity data and the negative polarity data.

In addition, the pre-processing unit 710 further includes an excitation profile measurement section 715 that measures excitation profiles of the positive polarity data and the negative polarity data and a phase difference optimum value search section 718 that searches for a value that minimizes an evaluation value by changing a first-order phase difference, which is a coefficient of a first-order term of a phase difference between the positive polarity data and the negative polarity data, and a zero-order phase difference, which is a zero-order term of the phase difference, from initial values set in advance according to a rule set in advance and determines optimal values of the zero-order phase difference and the first-order phase difference. The evaluation value is a signal amount of side lobe obtained from each of the excitation profiles. The refocusing pulse application amount calculation section 712 determines each refocusing pulse application amount using the first-order phase difference. The image reconstruction section 721 corrects a phase difference between the positive polarity data and the negative polarity data using the optimal value of the zero-order phase difference before the addition.

In addition, the phase difference optimum value search section 718 performs a process of fixing the zero-order phase difference to the optimal value of the zero-order phase difference, determining as the optimal value of the first-order phase difference a first-order phase difference that minimizes the evaluation value by changing the first-order phase difference according to a rule set in advance, fixing the first-order phase difference to the optimal value of the first-order phase difference, and determining as the optimal value of the zero-order phase difference a zero-order phase difference that minimizes the evaluation value by changing the zero-order phase difference according to a rule set in advance, until an evaluation value when the optimal value of the zero-order phase difference is obtained converges to a range set in advance.

That is, in the present embodiment, zero-order and first-order phase differences are searched for on the basis of the side lobe amount. For example, when the phase distribution of the excitation profile is distorted due to the influence of non-uniformity of the magnetic field and the like, the distribution of the phase difference between the positive polarity data and the negative polarity data draws a high-order curve. Thus, in the method of the present embodiment, when it is difficult to fit the first-order straight line to the phase distribution, that is, even when the phase distribution draws a high-order curve, it is possible to calculate the zero-order phase difference and the first-order phase difference that minimizes the signal amount of the side lobe. Therefore, since it is possible to obtain the good excitation profile with high accuracy regardless of the uniformity of the static magnetic field of the apparatus, it is possible to obtain a high-quality image.

In addition, in the present embodiment, the signal amount of the side lobe defined by Expression (25) is used as the evaluation value. Here, Expression (25) means calculating the amount of the signal in a range other than the main lobe in the excitation profile. Accordingly, as long as it is possible to check the signal amount other than the main lobe, it is possible to use other evaluation expressions (evaluation values) other than Expression (25). For example, it is possible to use an evaluation expression to normalize the side lobe amount with the signal amount of the main lobe. In addition, it is also possible to use an evaluation expression to calculate the side lobe amount by giving a weighting to the signal strength of the side lobe in proportion to the distance from the designated slice position.

In addition, in the present embodiment, when searching for the optimal values of the zero-order phase difference and the first-order phase difference, the zero-order phase difference and the first-order phase difference are changed by the fixed change amounts set in advance. However, the present invention is not limited thereto. For example, the zero-order phase difference and the first-order phase difference may be separately searched for using a search algorithm represented by the golden section method or the like. For example, the zero-order phase difference and the first-order phase difference may be searched for together using a multi-dimensional search algorithm represented by the downhill simplex method, the multi-dimensional conjugate gradient method, or the like.

In addition, also in the present embodiment, in the case of an MRI apparatus in which an excitation position shift is difficult to occur, it is not necessary to perform shift amount calculation and irradiation frequency calculation. That is, in this case, the shift amount calculation section 717 and the irradiation frequency calculation section 713 may not be provided. In this case, it is assumed that the irradiation frequency used in the main measurement is designated by the imaging parameter.

In addition, also in the present embodiment, when it is known that the zero-order phase difference does not significantly affect the image quality, it is not necessary to perform addition processing in consideration of the zero-order phase difference. In this case, the phase difference optimum value search section 718 may search for the optimal value of only the first-order phase difference. When the zero-order phase difference is not calculated, the phase difference is treated as a fixed value (for example, 0 [deg]).

In addition, also in the present embodiment, similar to the second embodiment, the pre-processing may be performed immediately before the main measurement, or may be performed at the time of installation work of the apparatus. When the pre-processing is performed at the time of installation work of the apparatus, the pre-processing is performed under the conditions of the combination of all slice positions and slice thicknesses designated in the main measurement processing. Alternatively, it is also possible to perform the pre-processing under only the representative conditions. In any case, the obtained result is stored in the storage device 172 or the like so as to match the calculation conditions.

Fourth Embodiment

Next, a fourth embodiment to which the present invention is applied will be described. The present embodiment is characterized in that the shift amount of the excitation position and the calculation accuracy of the first-order phase difference are improved by performing pre-processing multiple times.

Figure 22:
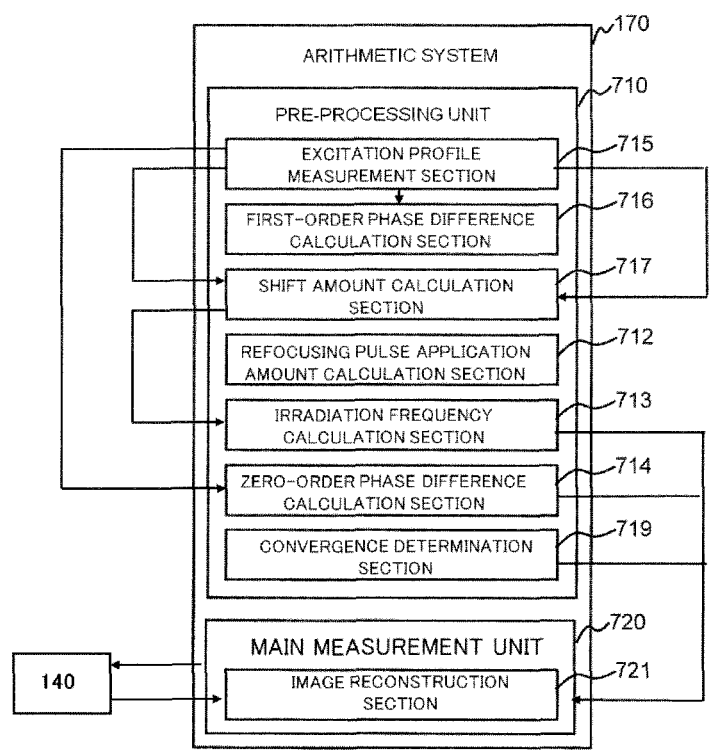
FIG. 22 is a functional block diagram of an arithmetic system of a fourth embodiment.

The MRI apparatus 100 of the present embodiment has basically the same configuration as in the first embodiment. In addition, the configuration of the arithmetic system 170 is basically the same as the configuration in the second embodiment. In the present embodiment, however, as shown in FIG. 22, the pre-processing unit 710 further includes a convergence determination section 719 in order to improve the calculation accuracy of the first-order phase difference and the shift amount by repeating the calculation of the first-order phase difference and the calculation of the shift amount.

In addition, the processing itself of the pre-processing unit 710 is also different.

The convergence determination section 719 of the present embodiment determines whether or not the first-order phase difference and the shift amount satisfy the convergence conditions set in advance whenever the first-order phase difference calculation section 716 and the shift amount calculation section 717 calculate the first-order phase difference and the shift amount.

The pre-processing unit 710 of the present embodiment advances processing according to the determination result. Specifically, when the determination result is No, the refocusing pulse application amount calculation section 712 is made to calculate the refocusing pulse application amount using the calculated first-order phase difference and the irradiation frequency calculation section 713 is made to calculate the irradiation frequency, and the excitation profile measurement section 715 is made to execute the excitation profile measurement sequence 500 to measure the excitation profile again using the refocusing pulse application amount and the irradiation frequency. On the other hand, when the determination result satisfies the convergence conditions, the zero-order phase difference calculation section is made to calculate a zero-order phase difference from the excitation profile used to calculate the first-order phase difference.

Figure 23:
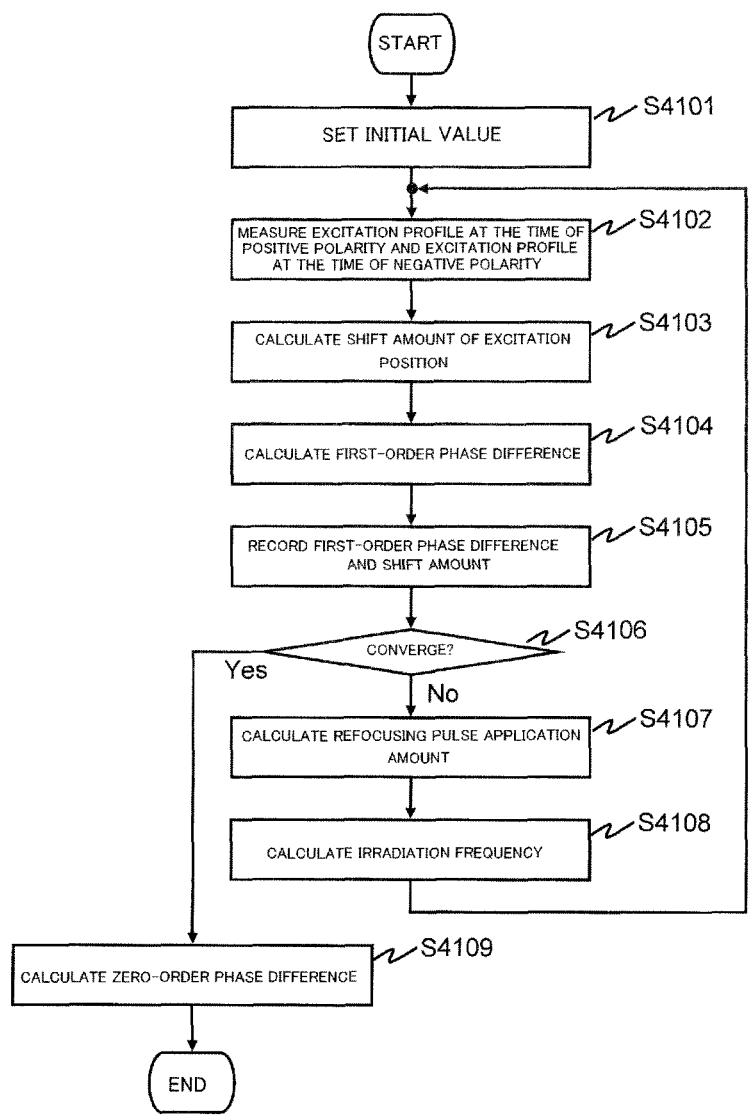
FIG. 23 is a flow chart of pre-processing of the fourth embodiment.

Hereinafter, the flow of the pre-processing of the pre-processing unit 710 of the present embodiment will be described with reference to FIG. 23. Here, one specific slice is extracted for explanation.

The pre-processing unit 710 of the present embodiment sets the refocusing pulse application amount and the irradiation frequency set by the imaging parameter (step S4101) Then, the excitation profile measurement section 715 executes the excitation profile measurement sequence 500 and measures the excitation profile at the time of positive polarity and the excitation profile at the time of negative polarity using the same method as in the second embodiment (step S4102).

Then, the shift amount calculation section 717 calculates the shift amount Shift of the excitation position according to Expressions (12) to (14) using the same method as in the second embodiment (step S4103). Then, the first-order phase difference calculation section calculates the first-order phase difference FirstOrderPhase according to Expressions (15) to (19) using the same method as in the second embodiment (step S4104).

Then, the pre-processing unit 710 stores the calculated Shift amount shift and first-order phase difference FirstOrderPhase in the storage device 172 so as to match the number of times of calculation (step S4105).

Then, from the second time, the convergence determination section 719 determines whether or not the convergence conditions are satisfied, that is, whether or not each value converges using the shift amount shift and the first-order phase difference FirstOrderPhase calculated this time and the excitation position shift amount shift and the first-order phase difference FirstOrderPhase calculated last (step S4106).

This determination is performed according to the following Expressions (33) and (34).

[Expression 33]
$$0.1 < \left(1 - \left|\frac{Shift(n)}{Shift(n-1)}\right|\right) \times 100 \quad (33)$$

[Expression 34]
$$0.1 < \left(1 - \left|\frac{FirstOrderPhase(n)}{FirstOrderPhase(n-1)}\right|\right) \times 100 \quad (34)$$

Here, Shift(n) is a shift amount recorded at the n-th time, and FirstOrderPhase(n) is a first-order phase recorded at the n-th time. In addition, Expressions (33) and (34) show the convergence conditions when each rate of change is less than 0.1[%] while repeating the calculation of the shift amount and the first-order phase.

In addition, in the determination processing, it is necessary to repeat the process at least twice for comparison with the value recorded in the last search.

When at least one of Expressions (33) and (34) is not satisfied, the convergence determination section 719 outputs No as a determination result. In response to this, the pre-processing unit 710 makes the refocusing pulse application amount calculation section 712 calculate the refocusing pulse application amount from the first-order phase difference FirstOrderPhase using Expressions (20) and (21) as in the second embodiment (step S4107). In addition, the irradiation frequency calculation section 713 is made to calculate the irradiation frequency from calculated shift amount Shift using Expressions (22) and (23) as in the second embodiment (step S4108). In addition, any of the irradiation frequency and the refocusing pulse application amount may be calculated first.

In addition, the pre-processing unit 710 sets the calculated irradiation frequency and refocusing pulse application amount in the excitation profile measurement sequence 500, and returns to step S4102 to repeat the processing.

On the other hand, when both Expressions (33) and (34) are satisfied in step S4106, the convergence determination section 719 outputs the determination result indicating that the convergence conditions are satisfied. In response to this, the pre-processing unit 710 ends the iterative process, and makes the zero-order phase difference calculation section 714 calculate the zero-order phase difference in the same method as in the second embodiment using the first-order phase difference FirstOrderPhase at that time and Expression (24) (step S4109).

In addition, since the main measurement processing of the present embodiment is the same as that in the first embodiment, explanation thereof will not be given herein.

As described above, according to the present embodiment, there is provided a magnetic resonance imaging apparatus including: a static magnetic field generation system 120; a measurement system including a gradient magnetic field generation system 130, a high frequency magnetic field generation system 150, and a high frequency magnetic field detection system 160; and an arithmetic system 170 that controls an operation of the measurement system according to a pulse sequence to measure a nuclear magnetic resonance signal and performs calculation using data obtained from the nuclear magnetic resonance signal. The pulse sequence is an ultra-short echo time sequence to obtain each echo signal by performing two slice selection excitations by inverting a polarity of a slice gradient magnetic field, which is applied together with a half RF pulse, between a positive polarity and a negative polarity. The arithmetic system 170 includes a pre-processing unit 710 that calculates a correction value used in the measurement and the calculation and a main measurement unit 720 that sets the correction value calculated by the pre-processing unit 710 in the pulse sequence and performs main measurement by controlling the measurement system according to the pulse sequence after the setting so that an image is reconstructed. The pre-processing unit 710 includes a refocusing pulse application amount calculation section 712 that calculates an application amount of a refocusing pulse of each slice gradient magnetic field as the correction value. The main measurement unit 720 includes an image reconstruction section 721 that adds positive polarity data, which is an echo signal obtained when the slice gradient magnetic field having a positive polarity is applied, and negative polarity data, which is an echo signal obtained when the slice gradient magnetic field having a negative polarity is applied, in the main measurement and reconstructs an image using polarity-added data after the addition. The refocusing pulse application amount calculation section 712 calculates the application amount of each refocusing pulse so as to reduce a side lobe signal of an excitation profile after adding the positive polarity data and the negative polarity data.

In addition, the pre-processing unit 710 further includes an excitation profile measurement section 715 that measures excitation profiles of the positive polarity data and the negative polarity data and a first-order phase difference calculation section 716 that calculates a coefficient of a first-order term of the phase difference as a first-order phase difference using the excitation profiles. The refocusing pulse application amount calculation section 712 determines the refocusing pulse application amount using the first-order phase difference.

In addition, the pre-processing unit 710 may further include an irradiation frequency calculation section 713 that calculates each irradiation frequency of the half RF pulse as the correction value and a shift amount calculation section 717 that calculates an excitation position shift amount between the excitation profiles. In this case, the irradiation frequency calculation section 713 calculates the irradiation frequency so as to eliminate a position shift between the two slice selection excitation positions, and the position shift is calculated using the shift amount.

In addition, the pre-processing unit 710 may further include a zero-order phase difference calculation section 714 that calculates a zero-order phase difference, which is a zero-order term of a phase difference between the positive polarity data and the negative polarity data, as the correction value. In this case, the zero-order phase difference calculation section 714 calculates the zero-order phase difference using each excitation profile. In addition, the image reconstruction section 721 corrects a phase difference between the positive polarity data and the negative polarity data using the zero-order phase difference before the addition.

In addition, the pre-processing unit 710 further includes a convergence determination section 719 that determines whether or not the first-order phase difference and the shift amount satisfy convergence conditions set in advance whenever the first-order phase difference calculation section and the shift amount calculation section calculate the first-order phase difference and the shift amount. When the determination result is negative, the refocusing pulse application amount calculation section 712 calculates the application amount and the irradiation frequency calculation section 713 calculates the irradiation frequency, the excitation profile measurement section 715 measures each of the excitation profiles when the calculated application amount and the calculated irradiation frequency are used, and the first-order phase difference calculation section calculates the first-order phase difference from the measurement result and the shift amount calculation section calculates the shift amount from the measurement result. When the determination result satisfies the convergence conditions, the zero-order phase difference calculation section 714 calculates the zero-order phase difference from each of the excitation profiles that are newest.

That is, according to the present embodiment, the optimal irradiation frequency and refocusing pulse application amount are determined while feeding back a calculation result to the pulse sequence. For example, when the pulse sequence is changed, the inclination of the first-order phase and the shift amount may not be able to be canceled out completely. According to the present embodiment, however, since repetitive processing is performed until the convergence conditions set in advance are satisfied, it is possible to calculate the more appropriate shift amount and first-order shift amount. Therefore, it is possible to obtain the more appropriate refocusing pulse application amount and irradiation frequency and reflect these in the pulse sequence.

Thus, according to the present embodiment, even if each error cannot be completely corrected in one calculation of the shift amount and the first-order phase, it is possible to calculate more accurate correction values by repetitive processing. Therefore, it is possible to acquire an image with higher quality.

In addition, the calculation of the zero-order phase difference is not included in the repetitive processing during the feedback processing of the first-order phase difference calculation and the shift amount calculation. This is because the zero-order phase is used in the reconstruction processing and this does not involve changing the pulse sequence. Therefore, according to the present embodiment, it is possible to determine the optimal pulse sequence and then calculate the zero-order phase difference according to the optimal pulse sequence and reflect the zero-order phase difference in the reconstruction of the image. Thus, according to the present embodiment, it is possible to calculate the optimal irradiation frequency, refocusing pulse cation amount, and zero-order phase difference efficiently.

In addition, although the convergence condition is defined in advance in the present embodiment, determination of convergence is not limited to this. For example, it is also possible to determine the first-order phase difference and the shift amount by repeating the process a fixed number of times without defining the convergence conditions and calculate the irradiation frequency and the refocusing pulse application amount.

In addition, also in the present embodiment, in the case of an MRI apparatus in which an excitation position shift is difficult to occur, it is not necessary to perform shift amount calculation and irradiation frequency calculation. In this case, therefore, the shift amount calculation section 717 and the irradiation frequency calculation section 713 may not be provided. In addition, in this case, the value of the variable Shift in Expression (15) to calculate the phase difference Phase_complex(x) is assumed to be 0. In addition, it is assumed that the irradiation frequency used in the main measurement is designated by the imaging parameter.

In addition, also in the present embodiment, when it is known that the zero-order phase difference does not significantly affect the image quality, it is not necessary to perform addition processing in consideration of the zero-order phase difference. In this case, the zero-order phase difference calculation section 713 may not be provided. When addition processing is not performed, 0 (deg) may be set as a phase difference.

In addition, although the case where the zero-order phase difference and the first-order phase difference are calculated using the method of the second embodiment has been described as an example in the present embodiment, the present invention is not limited thereto. For example, the zero-order phase difference and the first-order phase difference may be calculated using the method of the third embodiment. In this case, however, in the zero-order phase difference calculation process of step S4109, the zero-order phase difference is searched for in a state where the first-order phase difference is fixed to 0 [deg].

In addition, also in the present embodiment, similar to the second embodiment, the pre-processing may be performed immediately before the main measurement, or may be performed at the time of installation work of the apparatus. When the pre-processing is performed at the time of installation work of the apparatus, the pre-processing is performed under the conditions of the combination of all slice positions and slice thicknesses designated in the main measurement processing. Alternatively, it is also possible to perform the pre-processing under only the representative conditions. In any case, the obtained result is stored in the storage device 172 or the like so as to match the calculation conditions.

In addition, in each of the embodiments described above, various changes can also be made as described in the embodiments. In addition, the procedure of the flow chart shown for explanation of each embodiment is an example, and some processes may be omitted. In addition, other processes may be added as necessary.

As described above, according to each embodiment described above, when the phase distribution of the excitation profile is changed due to the influence of an eddy current of the slice gradient magnetic field and the influence of relaxation during half RF pulse irradiation in a UTE sequence and/or when the position of the intensity distribution of the excitation profile is shifted due to gradient magnetic field offset, the shift amount and zero-order and first-order phase differences of the excitation position between positive polarity data and negative polarity data can be calculated by measuring the waveform of the slice gradient magnetic field or the excitation profile. By setting the optimal irradiation frequency of the RF pulse and the optimal refocusing pulse application amount of the slice gradient magnetic field on the basis of the calculation result and adding a zero-order phase difference at the time of complex addition of the positive polarity data and the negative polarity data, it is possible to obtain a good excitation profile. As a result, a reconstructed image in which artifacts are suppressed can be obtained with signals from positions other than the designated slice position not being mixed into the reconstructed image.

In particular, this is effective for measurement using the multi-slice method that cannot suppress a side lobe signal of the excitation profile with the saturation pulse.

REFERENCE SIGNS LIST

100: MRI apparatus
101: object
120: static magnetic field generation system
130: gradient magnetic field generation system
131: gradient magnetic field coil
132: gradient magnetic field power source
140: sequencer
150: high frequency magnetic field generation system
151: transmission coil
152: synthesizer
153: modulator
154: high frequency amplifier
160: high frequency magnetic field detection system
161: receiving coil
162: signal amplifier
163: quadrature phase detector
164: A/D converter
170: arithmetic system
171: CPU
172: storage device
173: external storage device
174: display device
175: input device
200: UTE sequence
201: half RF pulse
202: half RF pulse
211: slice gradient magnetic field
211: positive polarity slice gradient magnetic field
212: slice gradient magnetic field
212: negative polarity slice gradient magnetic field
221: phase encoding gradient magnetic field
222: phase encoding gradient magnetic field
231: readout encoding gradient magnetic field
232: readout encoding gradient magnetic field
241: echo signal
251: refocusing pulse
252: refocusing pulse
301: excitation profile
302: excitation profile
303: excitation profile
311: phase distribution
312: phase distribution
313: phase distribution
321: designated slice gradient magnetic field waveform
322: slice gradient magnetic field measured waveform
331: down portion of slice gradient magnetic field
341: position where excitation is needed
342: excitation position
343: offset
411: measured waveform of positive polarity slice gradient magnetic field
412: measured waveform of negative polarity slice gradient magnetic field,
500: excitation profile measurement sequence
501: half RF pulse
502: half RF pulse
511: positive polarity slice gradient magnetic field
512: negative polarity slice gradient magnetic field
531: readout encoding gradient magnetic field
532: readout encoding gradient magnetic field
541: echo signal
542: echo signal
601: excitation profile at the time of positive polarity
602: excitation profile at the time of negative polarity
611: calculated phase distribution
612: phase distribution after phase unwrapping
620: center
621: phase change section
710: pre-processing unit
711: slice gradient magnetic field waveform measurement section
712: refocusing pulse application amount calculation section
713: irradiation frequency calculation section
713: irradiation frequency calculation section
714: zero-order phase difference calculation section
715: excitation profile measurement section
716: first-order phase difference calculation section
717: shift amount calculation section
718: phase difference optimum value search section
719: convergence determination section
720: main measurement unit
721: image reconstruction section
801: intensity distribution of positive polarity data excitation profile
802: intensity distribution of negative polarity data excitation profile
803: intensity distribution of polarity-added data excitation profile
813: intensity distribution of polarity-added data excitation profile
823: intensity distribution of polarity-added data excitation profile
833: intensity distribution of polarity-added data excitation profile
843: intensity distribution of polarity-added data excitation profile
853: intensity distribution of polarity-added data excitation profile
861: image
862: image
871: profile
872: profile

The invention claimed is:

1. A magnetic resonance imaging apparatus, comprising:
a static magnetic field generation system;
a measurement system including a gradient magnetic field generation system, a high frequency magnetic field generation system, and a high frequency magnetic field detection system; and
an arithmetic system that controls an operation of the measurement system according to a pulse sequence to measure a nuclear magnetic resonance signal and performs calculation using data obtained from the nuclear magnetic resonance signal,
wherein the pulse sequence is an ultra-short echo time sequence to obtain each echo signal by performing two slice selection excitations by inverting a polarity of a slice gradient magnetic field, which is applied together with a half RF pulse, between a positive polarity and a negative polarity, the arithmetic system includes a pre-processing unit that calculates a correction value used in the measurement and the calculation and a main measurement unit that sets the correction value calculated by the pre-processing unit in the pulse sequence, performs main measurement by controlling the measurement system according to the pulse sequence after the setting, and reconstructs an image, the pre-processing unit includes a refocusing pulse application amount calculation section that calculates an application amount of a refocusing pulse of each slice gradient magnetic field as the correction value, the main measurement unit includes an image reconstruction section that adds positive polarity data, which is an echo signal obtained when the slice gradient magnetic field having a positive polarity is applied, and negative polarity data, which is an echo signal obtained when the slice gradient magnetic field having a negative polarity is applied, in the main measurement and reconstructs the image using polarity-added data after the addition, and the refocusing pulse application amount calculation section calculates the application amount of each refocusing pulse so as to reduce a side lobe signal of an excitation profile obtained by adding the positive polarity data and the negative polarity data.

2. The magnetic resonance imaging apparatus according to claim 1,
wherein the pre-processing unit further includes an irradiation frequency calculation section that calculates each irradiation frequency of the half RF pulse as the correction value, and
the irradiation frequency calculation section calculates each irradiation frequency so as to eliminate a position shift between excitation positions by the two slice selection excitations.

3. The magnetic resonance imaging apparatus according to claim 1,
wherein the pre-processing unit further includes a zero-order phase difference calculation section that calculates a zero-order phase difference, which is a zero-order term of a phase difference between the positive polarity data and the negative polarity data, as the correction value, and
the image reconstruction section corrects the phase difference between the positive polarity data and the negative polarity data using the zero-order phase difference before the addition.

4. The magnetic resonance imaging apparatus according to claim 1,
wherein the pre-processing unit further includes an irradiation frequency calculation section that calculates an irradiation frequency of each half RF pulse as the correction value and a zero-order phase difference calculation section that calculates a zero-order phase difference, which is a zero-order term of a phase difference between the positive polarity data and the negative polarity data, as the correction value,
the irradiation frequency calculation section calculates each irradiation frequency so as to eliminate a position shift between excitation positions by the two slice selection excitations, and
the image reconstruction section corrects the phase difference between the positive polarity data and the negative polarity data using the zero-order phase difference before the addition.

5. The magnetic resonance imaging apparatus according to claim 1,
wherein the pre-processing unit further includes a slice gradient magnetic field waveform measurement section that measures a slice gradient magnetic field waveform of the pulse sequence, and
the refocusing pulse application amount calculation section calculates the application amount of each refocusing pulse using the measured slice gradient magnetic field waveform.

6. The magnetic resonance imaging apparatus according to claim 2,
wherein the pre-processing unit further includes a slice gradient magnetic field waveform measurement section that measures a slice gradient magnetic field waveform of the pulse sequence,
the refocusing pulse application amount calculation section calculates the application amount of each refocusing pulse using the measured slice gradient magnetic field waveform, and
the irradiation frequency calculation section calculates the position shift using a strength of a slice gradient magnetic field obtained from the measured slice gradient magnetic field waveform.

7. The magnetic resonance imaging apparatus according to claim 3,
wherein the pre-processing unit further includes a slice gradient magnetic field waveform measurement section that measures a slice gradient magnetic field waveform of the pulse sequence,
the refocusing pulse application amount calculation section calculates the application amount of each refocusing pulse using the measured slice gradient magnetic field waveform, and
the zero-order phase difference calculation section calculates the zero-order phase difference using a difference between a slice gradient magnetic field waveform in which the polarity is positive and a slice gradient magnetic field waveform in which the polarity is negative.

8. The magnetic resonance imaging apparatus according to claim 1,
wherein the pre-processing unit further includes an excitation profile measurement section that measures excitation profiles of the positive polarity data and the negative polarity data and a first-order phase difference calculation section that calculates a coefficient of a first-order term of the phase difference as a first-order phase difference using the excitation profiles, and
the refocusing pulse application amount calculation section determines each refocusing pulse application amount using the first-order phase difference.

9. The magnetic resonance imaging apparatus according to claim 2,
wherein the pre-processing unit further includes an excitation profile measurement section that measures excitation profiles of the positive polarity data and the negative polarity data, a first-order phase difference calculation section that calculates a coefficient of a first-order term of the phase difference as a first-order phase difference using the excitation profiles, and a shift amount calculation section that calculates an excitation position shift amount between the excitation profiles,
the refocusing pulse application amount calculation section determines each refocusing pulse application amount using the first-order phase difference, and the irradiation frequency calculation section determines the position shift using the shift amount.

10. The magnetic resonance imaging apparatus according to claim 3,
wherein the pre-processing unit further includes an excitation profile measurement section that measures excitation profiles of the positive polarity data and the negative polarity data and a first-order phase difference calculation section that calculates a coefficient of a first-order term of the phase difference as a first-order phase difference using the excitation profiles,
the refocusing pulse application amount calculation section determines each refocusing pulse application amount using the first-order phase difference, and
the zero-order phase difference calculation section calculates the zero-order phase difference using each of the excitation profiles.

11. The magnetic resonance imaging apparatus according to claim 4,
wherein the pre-processing unit further includes an excitation profile measurement section that measures excitation profiles of the positive polarity data and the negative polarity data, a first-order phase difference calculation section that calculates a coefficient of a first-order term of the phase difference as a first-order phase difference using the excitation profiles, and a shift amount calculation section that calculates an excitation position shift amount between the excitation profiles,
the refocusing pulse application amount calculation section determines each refocusing pulse application amount using the first-order phase difference,
the irradiation frequency calculation section determines the position shift using the shift amount, and
the zero-order phase difference calculation section calculates the zero-order phase difference using each of the excitation profiles.

12. The magnetic resonance imaging apparatus according to claim 1,
wherein the pre-processing unit further includes an excitation profile measurement section that measures excitation profiles of the positive polarity data and the negative polarity data and a phase difference optimum value search section that searches for a value that minimizes an evaluation value by changing a first-order phase difference, which is a coefficient of a first-order term of a phase difference between the positive polarity data and the negative polarity data, and a zero-order phase difference, which is a zero-order term of the phase difference, from initial values set in advance according to a rule set in advance and determines optimal values of the zero-order phase difference and the first-order phase difference,
the evaluation value is a signal amount of side lobe obtained from each of the excitation profiles,
the refocusing pulse application amount calculation section determines each refocusing pulse application amount using the first-order phase difference, and
the image reconstruction section corrects a phase difference between the positive polarity data and the negative polarity data using the optimal value of the zero-order phase difference before the addition.

13. The magnetic resonance imaging apparatus according to claim 12,
wherein the phase difference optimum value search section performs a process of fixing the zero-order phase difference to the optimal value of the zero-order phase difference, determining as the optimal value of the first-order phase difference a first-order phase difference that minimizes the evaluation value obtained by changing the first-order phase difference according to a rule set in advance, fixing the first-order phase difference to the optimal value of the first-order phase difference, and determining as the optimal value of the zero-order phase difference a zero-order phase difference that minimizes the evaluation value obtained by changing the zero-order phase difference according to a rule set in advance, until an evaluation value when the optimal value of the zero-order phase difference is obtained converges to a range set in advance.

14. The magnetic resonance imaging apparatus according to claim 8,
wherein the pre-processing unit further includes a convergence determination section that determines whether or not the first-order phase difference satisfies convergence conditions set in advance whenever the first-order phase difference calculation section calculates the first-order phase difference, and
when the determination result is negative, the refocusing pulse application amount calculation section calculates the application amount, the excitation profile measurement section measures each of the excitation profiles when the calculated application amount is used, and the first-order phase difference calculation section calculates the first-order phase difference from the measurement result.

15. The magnetic resonance imaging apparatus according to claim 9,
wherein the pre-processing unit further includes a convergence determination section that determines whether or not the first-order phase difference and the shift amount satisfy convergence conditions set in advance whenever the first-order phase difference calculation section and the shift amount calculation section calculate the first-order phase difference and the shift amount, and
when the determination result is negative, the refocusing pulse application amount calculation section calculates the application amount and the irradiation frequency calculation section calculates the irradiation frequency, the excitation profile measurement section measures each of the excitation profiles when the calculated application amount and the calculated irradiation frequency are used, and the first-order phase difference calculation section calculates the first-order phase difference from the measurement result and the shift amount calculation section calculates the shift amount from the measurement result.

16. The magnetic resonance imaging apparatus according to claim 10,
wherein the pre-processing unit further includes a convergence determination section that determines whether or not the first-order phase difference satisfies convergence conditions set in advance whenever the first-order phase difference calculation section calculates the first-order phase difference,
when the determination result is negative, the refocusing pulse application amount calculation section calculates the application amount, the excitation profile measurement section measures each of the excitation profiles when the calculated application amount is used, and the first-order phase difference calculation section calculates the first-order phase difference from the measurement result, and when the determination result satisfies the convergence conditions, the zero-order phase difference calculation section calculates the zero-order phase difference from each of the excitation profiles that are newest.

17. The magnetic resonance imaging apparatus according to claim 11, wherein the pre-processing unit further includes a convergence determination section that determines whether or not the first-order phase difference and the shift amount satisfy convergence conditions set in advance whenever the first-order phase difference calculation section and the shift amount calculation section calculate the first-order phase difference and the shift amount, when the determination result is negative, the refocusing pulse application amount calculation section calculates the application amount and the irradiation frequency calculation section calculates the irradiation frequency, the excitation profile measurement section measures each of the excitation profiles when the calculated application amount and the calculated irradiation frequency are used, and the first-order phase difference calculation section calculates the first-order phase difference from the measurement result and the shift amount calculation section calculates the shift amount from the measurement result, and when the determination result satisfies the convergence conditions, the zero-order phase difference calculation section calculates the zero-order phase difference from each of the excitation profiles that are newest.

18. The magnetic resonance imaging apparatus according to claim 4, wherein the main measurement is a multi-slice measurement, and the pre-processing unit determines the application amount of the refocusing pulse, the irradiation frequency, and the zero-order phase difference, which are used in the main measurement, for each slice position to be measured.

19. A correction value calculating method of calculating a correction value used in imaging based on an ultra-short echo time sequence to obtain each echo signal by performing two slice selection excitations by inverting a polarity of a slice gradient magnetic field, which is applied together with a half RF pulse, between a positive polarity and a negative polarity, the method comprising:

a pre-processing step of determining the correction value;

a measurement step of obtaining positive polarity data, which is an echo signal obtained when the slice gradient magnetic field having a positive polarity is applied, and negative polarity data, which is an echo signal obtained when the slice gradient magnetic field having a negative polarity is applied, by executing the ultra-short echo time sequence using the correction value determined in the pre-processing step; and an image reconstruction step of adding the positive polarity data and the negative polarity data and reconstructing an image using polarity-added data after made by the addition of the positive polarity data and the negative polarity data, wherein the pre-processing step includes a refocusing pulse application amount determination step of determining an application amount of a refocusing pulse to refocus the slice gradient magnetic field as the correction value, and in the refocusing pulse application amount determination step, the application amount of the refocusing pulse is determined so as to reduce a side lobe signal of an excitation profile after adding the positive polarity data and the negative polarity data.

20. The correction value calculating method according to claim 19, wherein the pre-processing step further includes an irradiation frequency calculation step of calculating an irradiation frequency of each half RF pulse as the correction value and a zero-order phase difference calculation step of calculating a zero-order phase difference, which is a zero-order term of a phase difference between the positive polarity data and the negative polarity data, as the correction value, in the irradiation frequency calculation step, each irradiation frequency is calculated so as to eliminate a position shift between positions by the two slice selection excitations, and in the image reconstruction step, a phase difference between the positive polarity data and the negative polarity data is corrected using the zero-order phase difference before the addition.

* * * * *